(12) United States Patent
Yamamoto et al.

(10) Patent No.: US 8,652,774 B2
(45) Date of Patent: Feb. 18, 2014

(54) AUTOMATED METHOD OF MANUFACTURING POLYER ARRAYS

(75) Inventors: Melvin Yamamoto, Fremont, CA (US); Clifford A. Oostman, Jr., Quilcene, WA (US); John S. Sze, Saratoga, CA (US); Keith S. Pearson, Campbell, CA (US); Philip C. Trenholme, Santa Cruz, CA (US); Dan Liu, Sunnyvale, CA (US); Chi Sou Yu, Saratoga, CA (US)

(73) Assignee: Affymetrix, Inc., Santa Clara, CA (US)

( * ) Notice: Subject to any disclaimer, the term of this patent is extended or adjusted under 35 U.S.C. 154(b) by 1497 days.

(21) Appl. No.: 11/243,621

(22) Filed: Oct. 4, 2005

(65) Prior Publication Data
US 2006/0088863 A1    Apr. 27, 2006

Related U.S. Application Data

(63) Continuation-in-part of application No. 10/826,577, filed on Apr. 16, 2004, now abandoned.

(60) Provisional application No. 60/463,563, filed on Apr. 16, 2003, provisional application No. 60/623,191, filed on Oct. 29, 2004, provisional application No. 60/703,706, filed on Jul. 29, 2005.

(51) Int. Cl.
*C12Q 1/68* (2006.01)

(52) U.S. Cl.
CPC ................................ *C12Q 1/6883* (2013.01)
USPC .................................... 435/6.1; 435/287.2

(58) Field of Classification Search
USPC ................... 435/6.1, 287.2; 257/76
See application file for complete search history.

(56) References Cited

U.S. PATENT DOCUMENTS

| | | | | |
|---|---|---|---|---|
| 5,628,110 | A * | 5/1997 | Sakaguchi et al. | 29/840 |
| 6,200,134 | B1 * | 3/2001 | Kovac et al. | 433/29 |
| 6,905,816 | B2 * | 6/2005 | Jacobs et al. | 435/5 |
| 2003/0049862 | A1 * | 3/2003 | He et al. | 436/180 |
| 2003/0082587 | A1 * | 5/2003 | Seul et al. | 435/6 |
| 2004/0038388 | A1 * | 2/2004 | Yamamoto et al. | 435/287.2 |

FOREIGN PATENT DOCUMENTS

WO      WO 9955460 A1 * 11/1999 ............... B01L 3/02

* cited by examiner

*Primary Examiner* — Michael Hobbs
(74) *Attorney, Agent, or Firm* — Affymetrix, Inc.

(57) ABSTRACT

The present invention provides methods to process multiple sensors by providing a sensor plate and HT plates. In a preferred embodiment of the invention, methods for assembling microarray pegs and microarray plates are described for high throughput microarray processing.

11 Claims, 12 Drawing Sheets

103

103

100

100

100

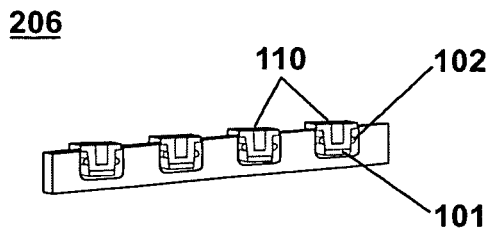
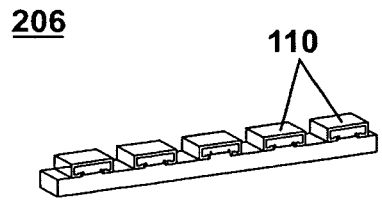
Fig. 7A          Fig. 7B
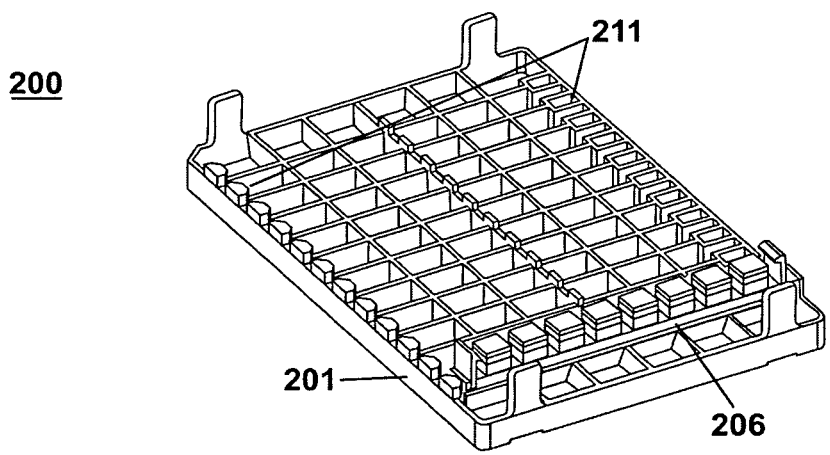
Fig. 8A
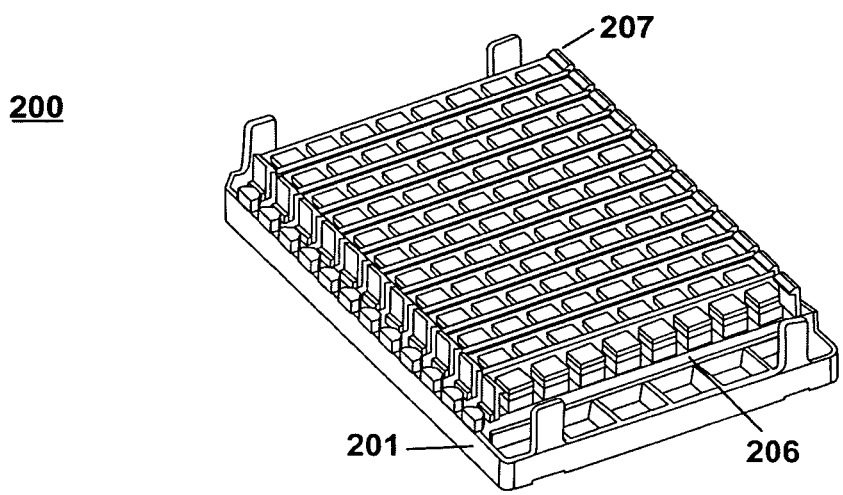
Fig. 8B

AUTOMATED METHOD OF MANUFACTURING POLYER ARRAYS

RELATED APPLICATIONS

The present application claims priority to U.S. provisional application Ser. No. 60/623,191, filed on Oct. 29, 2004, and to U.S. provisional application Ser. No. 60/703,706, filed on Jul. 29, 2005. The present application is also a continuation-in-part of U.S. patent application Ser. No. 10/826,577, filed on Apr. 16, 2004, which claims priority to U.S. Provisional Application Ser. No. 60/463,563, filed on Apr. 16, 2003. The '563, '577, '191, and '706 applications are incorporated herein by reference in their entirety for all purposes.

FIELD OF INVENTION

One aspect of the present invention relates to sensors and sensor packages. More particularly, one aspect of the present invention relates to the manufacturing and packaging of biological microarrays. In accordance with one aspect of the present invention, automated manufacturing methods are provided for the fabrication of high density polymer arrays and assortments of high density arrays. In particular, one aspect of the instant invention relates to the flexibility of an automated line to assemble various types of sensors into various types of packages. Another aspect of the present invention relates to an assembly method utilizing the tool for aligning the array to the package. More specifically, one aspect of the present invention relates to an assembly process consisting of dispensing and curing an adhesive to bond the sensor and package together.

BACKGROUND OF THE INVENTION

Methods have been developed for producing high density microarrays. These microarrays have wide ranging applications and are of great importance to the pharmaceutical, biotechnology and medical industries.

Arrays of nucleic acid probes can be used to extract sequence information from nucleic acid samples. The samples are exposed to the probes under conditions that allow hybridization. The arrays are then scanned to determine to which probes the sample molecules have hybridized. One can obtain sequence information by selective tiling of the probes with particular sequences on the arrays, and using algorithms to compare patterns of hybridization and non-hybridization. This method is useful for sequencing nucleic acids. It is also useful in diagnostic screening for genetic diseases or for the presence of a particular pathogen or a strain of pathogen.

The field of nucleic acid assays has been transformed by microarrays which allow monitoring of gene expression events, expression profiling, diagnostic and genotyping analyses, among other applications. Substrates bearing arrays of probes (fragments of nucleic acids) need to be produced/manufactured in a manner that allows assays such as expression monitoring, genotyping and other studies to be performed accurately and efficiently. With more sensitive applications being contemplated for microarrays in the fields of pharmacogenomics and diagnostics, for example, there exists a need in the art for additional devices for manufacturing and processing of microarrays.

SUMMARY OF THE INVENTION

According to one aspect of the present invention, a method is provided for constructing a sensor plate. A plurality of sensors is produced by dicing a substrate. Support members having a first end and a second end and plates are provided. First, a sensor from the diced substrate is attached to the first end of the support member. Next, the second end of the support member is attached to a plate. These steps are repeated until the desired sensor plate is produced. In a preferred embodiment, the sensors are microarrays and the support members are pegs. In another aspect of the present invention, the constructing method for a sensor plate further includes the attaching steps as bonding steps that use a curable low fluorescence adhesive.

According to one aspect of the invention, a method is provided for curing an adhesive during assembly of a sensor comprising a solid state narrow wavelength light source. Preferably, the solid state narrow wavelength light source is a blue LED having a wavelength which is from 430 nm to 480 nm and most preferably, the wavelength is approximately 455 nm.

According to one aspect of the invention, an apparatus is provided to reduce pitch and roll variations used during an assembly of a sensor package. The apparatus which has an x axis plane, y axis plane, and a z axis plane also has a plurality of adjustable kinematic features. One of the adjustable features is a fine pitch adjuster that transverses in the z axis plane. Other adjustable features are spherical kinematic features which are fixed in the nominal z axis plane and provide for rotation around the x and y axes by adjusting the adjustable features to reduce the pitch and roll variations of the sensor package to be assembled. According to another aspect of the invention, a method is provided for wherein the pluralities of adjustable kinematic features are adjusted at the same time. More preferably, an adjustable kinematic feature is a threaded mechanical device.

According to one aspect of the present invention, a flexible automated system is provided for assembling various types of sensors and packages. A plurality of sensors, a plurality of holding devices and a plurality of functional modules are provided. The modules have a common platform and at least one unique assembly step. The plurality of functional modules is connected to assemble a sensor to a holding device wherein a combination of various functional modules dictates which sensor and package are being assembled. The automated system is controlled by the software to assemble various types of sensors and packages.

According to another aspect of the invention, a method has at least one type of sensor and a plurality of different holding devices. In a preferred embodiment, the sensor is an array and the holding devices are cartridges and plates. In another preferred embodiment, the combined functional modules are an assembly, a bonding, and a final inspection module.

BRIEF DESCRIPTION OF THE DRAWINGS

The accompanying drawings, which are incorporated in and form a part of this specification, illustrate embodiments of the invention and, together with the description, serve to explain various aspects of the invention:

FIG. 1 depicts examples of a sensor peg.

FIG. 2 depicts various shapes of a support member.

FIG. 3 depicts a sensor cartridge designed for front-side scanning.

FIG. 4 depicts a sensor cartridge designed for back-side scanning.

FIG. 6 depicts a sensor strip with sensor pegs.

FIG. 7 depicts a sensor strip with sensor cartridges. FIG. 7A shows an uncovered sensor strip and FIG. 7B shows a covered sensor strip with sensor cartridges.

FIG. 8 depicts a sensor plate with at least one sensor strip. FIG. 8A shows a sensor plate with one sensor strip and FIG. 8B shows a full sensor plate with one cover off of one sensor strip.

FIG. 10 depicts a hybridization plate.

FIG. 13 depicts a wash plate.

FIG. 14 depicts a detection plate.

FIG. 15 depicts a package plate.

FIG. 17A shows a system to manufacture a microarray cartridge and FIG. 17B shows details of the assembly module displayed in FIG. 17A.

DETAILED DESCRIPTION OF THE INVENTION

I. General

Figure 1A:
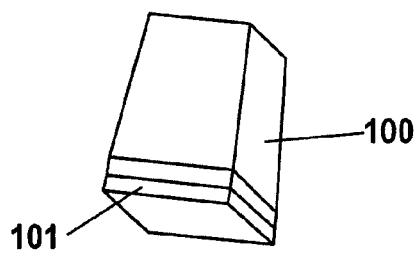
FIG. 1A shows a sensor peg which is an assembly of the support member of FIG. 2A with a sensor.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being, but may also be other organisms including, but not limited to, mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "Oligonucleotide Synthesis: A Practical Approach" 1984, IRL Press, London, Nelson and Cox (2000), *Lehninger, Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252, 743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. patent application Publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871, 928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, for example, *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159, 4,965, 188, and 5,333,675, each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA,* 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5, 413,909, 5,861, 245) and nucleic acid based sequence amplification (NABSA). (See, U.S. Pat. Nos. 5,409,818, 5,554,517, and 6,063,603, each of which is incorporated herein by reference). Other amplification methods that may be used are described in U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Ser. Nos. 09/916,135, 09/920,491 (U.S. patent application Publication 20030096235), Ser. No. 09/910,292 (U.S. patent application Publication 20030082543), and Ser. No. 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (2$^{nd}$ Ed. Cold Spring Harbor, N.Y., 1989); Berger and Kimmel *Methods in Enzymology*, Vol. 152, *Guide to Molecular Cloning Techniques* (Academic Press, Inc., San Diego, Calif., 1987); Young and Davis, *P.N.A.S,* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,225,625 in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758, 5,856,092, 5,902,723, 5,936,324, 5,981,956, 6,025,601, 6,090,555, 6,141,096, 6,185,030, 6,201,639; 6,218,803; and 6,225,625, in U.S. Ser. Nos. 10/389,194, 60/493,495 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of a method of the invention. Suitable computer readable medium include floppy disk, CD-ROM/DVD/DVD-ROM, hard-disk drive, flash memory, ROM/RAM, magnetic tapes, etc. The computer-executable instructions may be written in a suitable computer language or combination of several languages. Basic computational biology methods are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology,* (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., 2$^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/197,621, 10/063,559 (U.S. Publication No. 20020183936), Ser. Nos. 10/065,856, 10/065,868, 10/328, 818, 10/328,872, 10/423,403, and 60/482,389.

II. DEFINITIONS

The term "detection plate" as used herein refers to a body having at least two wells and at least one optically transparent window. A detection plate is a device used during the identification of the hybridization events on a plurality of sensors, such as from a sensor plate. Taking a sensor plate as an example, the corresponding detection plate is designed to receive the sensor plate. In one embodiment, the wells are filled with solution such that the sensors from the sensor plate are submerged when the sensor plate and the detection plates are assembled. The scanning of the sensors is performed through the optically transparent window which can be made from a low-fluorescence material such as fused silica, Zeonor (Nionex), etc. Optionally, a detection plate can have a physical barrier resistant to the passage of liquids around the individual wells or around a plurality of wells.

The term "sensor" and "biosensor" as used herein are used interchangeably and refer to a device that detects biological substances. A sensor is an analytical device having a biological recognition element e.g. enzyme, receptor, molecule, DNA, antibody, or microorganism in intimate contact with an electrochemical, optical, thermal, or acoustic signal transducer that together permit analysis of chemical properties or quantities. A sensor is a device which enables the monitoring of, for example, molecules, viruses, bacteria, and cells.

The term "sensor peg" as used herein refers to a device having a sensor that is attached to a support member or a peg. In one embodiment, a support member or peg is suitable to hold a sensor into a body wherein a corresponding liquid reaction of the sensor can occur for example, sensor pegs can be incorporated into the design of cartridges and sensor plates. Optionally, a peg can act like a handle or mechanism to facilitate the handling and assembly of a sensor.

The term "sensor plate" as used herein refers to a body having a plurality of sensors. The sensors are separated from each other such that each sensor can be processed separately if desired. In one embodiment, individual sensors or a plurality of sensors on the sensor plate can be separated by a physical barrier resistant to the passage of liquids. One example of a physical barrier can be in a form of an area or space, referred to as a well, capable of containing liquids in contact with the sensor. Another example of a physical barrier can be in a form of a gasket or any of a wide variety of seals to prevent the escape of a gas or fluid. Optionally, the sensors can be attached to the body by support members. The sensor plate can also be referred to by a name based on the type of sensor. For example, if the sensors on a sensor plate are microarrays, then the plate can be referred to as a microarray plate, DNA plate, and oligonucleotide plate.

The term "solid support", "support", and "substrate" as used herein are used interchangeably and refer to a material or group of materials having a rigid, semi-rigid surface or flexible surface. In one embodiment, the surface may be a combination of materials where at least one layer is flexible. Surfaces on the solid substrate can be composed of the same material as the substrate. In another embodiment, the substrate may be fabricated form a single material or be fabricated of two or more materials. Thus, the surface may be composed of any of a wide variety of materials, for example, polymers, plastics, resins, polysaccharides, silica or silica-based materials, carbon, metals, inorganic glasses, membranes, or any of the above-listed substrate materials. In a further embodiment, the surface can be supported by a flexible material or a solid material. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates, which are hereby incorporated by reference herein in its entirety for all purpose.

The term "support member" and "peg" as used herein are used interchangeably and refer to a "support" that projects a material of interest from a surface which the peg can be attached. The peg can be made of various materials and can take on various forms as described above under the "support" definition.

The term "monomer" as used herein refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. Different basis sets of monomers may be used at successive steps in the synthesis of a polymer. The term "monomer" also refers to a chemical subunit that can be combined with a different chemical subunit to form a compound larger than either subunit alone.

The term "shipping plate" as used herein refers to a device with at least two wells suitable for protecting at least two sensors. The shipping plate is a device used during the handling and shipping of the sensors, such as on a sensor plate. The shipping plate is designed to receive the sensor plate. Once the sensor plate is assembled and inspected, the shipping plate is assembled with the sensor plate. Optionally, the shipping plate can have a physical barrier resistant to the passage of liquids and gases around the individual wells or around a plurality of wells. Optionally, the shipping plates can have features to allow multiple sensor plates to be on top of each other.

The term "stain plate" as used herein refers to a device with at least two wells suitable for staining. In a preferred embodiment, the well depth is optimized to use the minimum volume of sample that is desired. The stain plate is a device used during an assay of the sensors, in particular the staining step for a plurality of sensors, such as on a sensor plate. Taking the sensor plate as an example, the corresponding stain plate is designed to receive the sensor plate. In one embodiment, after the stain solution is deposited into the wells of the stain plate, the sensor plate is assembled with the stain plate such that the active surfaces of the sensors are submerged into the stain solution. Optionally, the stain plate can have a physical barrier resistant to the passage of liquids and gases around the individual wells or around a plurality of wells.

The term "wash plate" as used herein refers to a device with at least two wells suitable for washing. In a preferred embodiment, the well depth and design is optimized to efficiently wash the sensor w/the optimal volume. The wash plate is a device used during an assay of the sensors, in particular the washing step for a plurality of sensors, such as on a sensor plate. Taking the sensor plate as an example, the corresponding wash plate is designed to receive the sensor plate. In one embodiment, after the washing solution is deposited into the wells of the wash plate, the sensor plate is assembled such that the active surfaces of the sensors are submerged into the washing solution. Optionally, the wash plate can have a physical barrier resistant to the passage of liquids and gases around the individual wells or around a plurality of wells.

III. Sensor Packages Having Sensor Pegs

In one aspect of the present invention, methods and apparatus for packaging sensors are provided. These methods and apparatus are particularly useful for packaging microarrays. The following describes the exemplary design, materials, manufacturing processes and application protocols used for processing a sensor peg as an illustration of the various aspect of the invention.

Sensor Peg

Figure 1B:
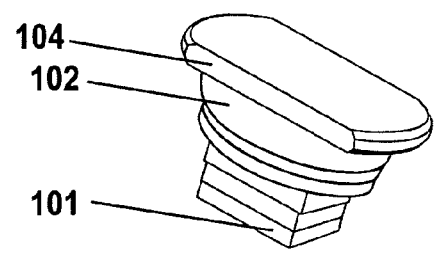
FIG. 1B depicts a sensor peg which includes an o-ring.
Figure 2A:
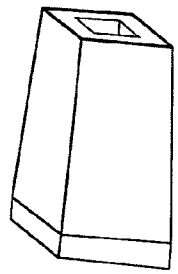
FIG. 2A shows a support member with tapered sides from narrow to wide wherein the sensor can be attached to the larger surface area.
Figure 2B:
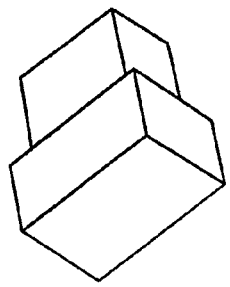
FIG. 2B depicts a support member with a block post and block platform in which the sensor can be attached to either end.
Figure 2C:
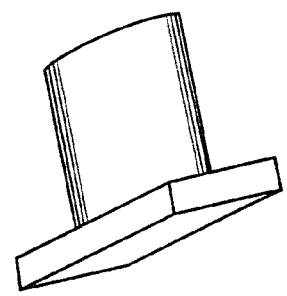
FIG. 2C depicts a support member with a cylindrical post and a square platform in which the sensor can be attached.

According to one aspect of the present invention, a sensor peg (103) as depicted in FIGS. 1A and 1B includes a support member (100) wherein the support member has at least one sensor (101) and is attached to an end of the support member. A support member can be formed as part of the holding device by machining, molding, and the like. A support member can also be formed separately and then attached by fasteners, bonding, ultrasonic welding, and the like. A support member material can be made from any material that is compatible with the chemical reactants, other operating environment (such as temperature) and solvents that are placed in the wells. The material of a support member can be different than the material of the sensor. Any of a variety of organic or inorganic materials or combinations thereof, may be employed for a support member including, for example, metal, plastics, such as polypropylene, polystyrene, polyvinyl chloride, polycarbonate, polysulfone, etc.; nylon; PTFE, ceramic; silicon; (fused) silica, quartz or glass, and the like. A support member may be solid, semi-rigid, flexible or a combination there of and be of any shape. The shape of a support member may be, for example, rectangular, diamond, square, circular, oval, any modifications thereof and so forth. Examples of different shaped support members (100) are shown in FIGS. 2A-2C. A support member (100) can be solid or hollow or partially hollow and the sensor can be attached at either side. The shape and size of one end of a support member (100) where a sensor is attached can be similar to that of the sensor. By way of illustration and not limitation, the dimensions of a support member (100) are about 0.5 mm to about 15 mm in length, width and depth.

In another preferred embodiment, pegs (100) are designed and assembled to allow a plurality of sensors to be processed at one time. The dimensions of a peg can depend on the size of the sensor, the number of sensors to be processed at one time and the method and apparatus used for further processing. For example, some process steps may require the sensor to be submerged into a well containing liquid and the formation of unwanted bubbles may appear. There are several ways in which bubbles can be created. For example, bubbles can be created during an insertion of a support member and sensor, sometimes referred to as a sensor peg, and bubbles may appear during the introduction of a liquid into the well. In some cases, a heat source is employed to provide appropriate hybridization temperature. Heating of the sample may also create bubbles. There are several ways to prevent the formation of bubbles, ie. degassing of the solution, redesign of receiving chamber, hydrophobic/hydrophilic coatings, design of the wells, etc. In one aspect of the invention, another method to reduce bubbles is provided by modifying the structure of the support member. The support member with sloped side walls are provided to reduce bubbles in a liquid sample during contact with the sensor and mixing of a liquid sample. In one embodiment, the support member is sloped such that the top is narrow and then widens at the bottom of the support member where the sensor is attached, see FIG. 1A. This may allow sufficient volume for gas to expand such that the bubbles diffuse at the surface of the liquid.

The methods and apparatus are suitable for various types of sensors, such sensors may include "nucleic acid sensors" such as nucleic acid microarrays. In a preferred embodiment, the sensor can be a microarray such as a cDNA array, a peptide array, a bead array or an in situ synthesized high density oligonucleotide array. The microarrays can include a substrate. In a preferred embodiment the substrate is a flat glass or silica. Surfaces on the solid substrate may be composed of the same material as the substrate or a different material. Thus, the surface may be composed of any of a wide variety of materials, for example, polymers, plastics, resins, polysaccharides, silica or silica-based materials, carbon, metals, inorganic glasses, membranes, or any of the above-listed substrate materials. In one embodiment, the surface will be optically transparent and will have surface SI—OH functionalities, such as those found on silica surfaces. The sensor peg can further include a sensor wherein the sensor is a microarray. In one embodiment of the present invention, a microarray peg (103) is provided wherein the support member (100) has sloped walls as mentioned in the previous section to assist in eliminating bubbles and where the end of the support member is shaped as a square to fit the sensor which is a microarray (101) as shown in FIG. 1A. In another preferred embodiment of the invention, a microarray peg (103) is provided wherein the support member includes a component which assists in the seal during a hybridization process, for example, an o-ring (102). In one aspect of the present invention, a micoarray peg (103) is provided wherein the support member includes a component to assist in the depth at which the sensor is placed into solution, for example a ledge(104) as illustrated in FIG. 1B.

Sensor Cartridge

Figure 3A:
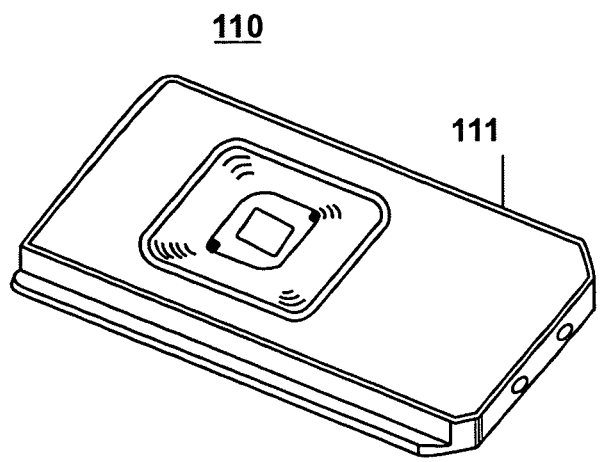
FIG. 3A shows the front view and FIG. 3B shows a cross section view of the sensor cartridge designed for front-side scanning.
Figure 3B:
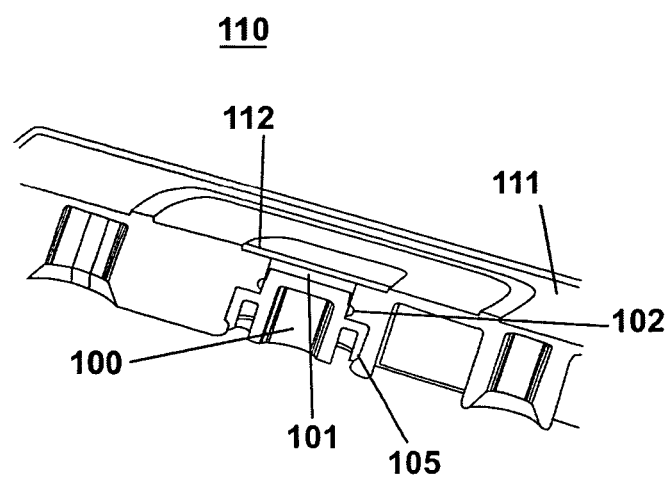

According to one aspect of the invention, a sensor cartridge (110) as depicted in FIGS. 3A and 3B, includes a housing (111) wherein the housing contains at least one sensor peg (103). In one preferred embodiment, the sensor cartridge further includes a sensor (101) wherein the sensor is a microarray which is attached to the end of the support member (100). In another preferred embodiment, the sensor peg includes a sealing mechanism (102) or a physical barrier resistant to the passage of liquids. One example of a physical barrier can be in a form of a gasket or any of a wide variety of seals to prevent the escape of a gas or fluid. In another preferred embodiment, the sensor peg includes a snapping mechanism. A snapping mechanism can include a variety of assembly methods that assembles components together. An example of a snapping mechanism is shown in FIG. 3B, where a part of the peg (105) is used to snap the sensor peg into place in the cartridge.

In one embodiment, a sensor cartridge utilizes two or more different types of scanning mechanism: front-side or back-side scanning. Front-side scanning is where the scanning is performed by scanning from the active surface of an array. The scanning process may be performed while the array is in a buffer solution. In this situation, the scan could be performed through a window and possibly some buffer. Back-side scanning, on the other hand, is where the scan is performed from the back of an array. For example, back-side scanning can be performed where an array is made on a transparent substrate such that the scanner scans through the substrate. In some instances, the substrate can also be used to contain a buffer solution. An example of a sensor cartridge which utilizes front-side scanning is shown in FIGS. 3A and 3B. A piece of transparent material (112) (for example, plastic, glass, etc.) is used to contain the buffer and provide a mechanism to scan the probes on the array. FIG. 3B shows the sensor peg indicated by the sensor (101) and the support member (100) within the housing (111). The active area of the sensor is facing out from the support member and into the chamber of the cartridge which contains a window (112). The scanning can be performed through the window while the buffer is contained within the cartridge. This type of sensor cartridge can utilize the maximum surface area of the sensor for scanning since the surface of the active area of the sensor can be fully exposed.

Figure 4A:
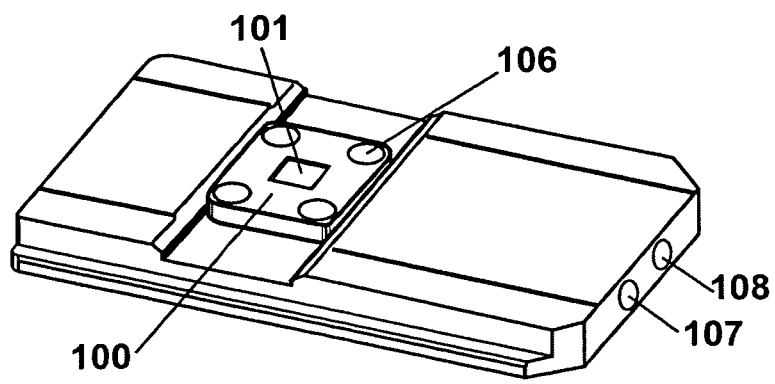
FIG. 4A shows the front view and FIG. 4B shows a cross section view of the sensor cartridge designed for back-side scanning.
Figure 4B:
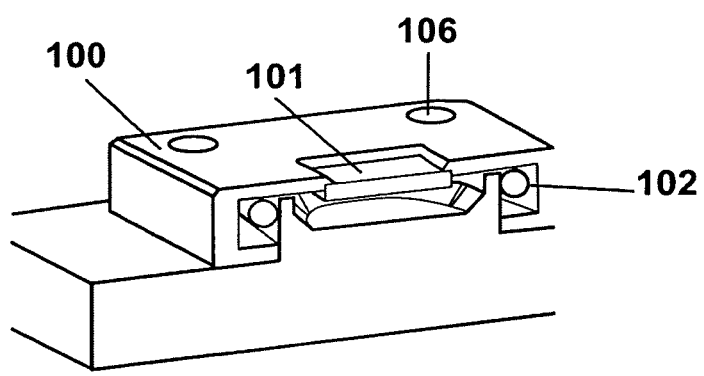

In a preferred embodiment of the invention, the sensor cartridge includes a sensor (101) attached to the end of a support member (100), having the active side facing down onto the support member (FIG. 4A). In this configuration, the wall of the support member can form a space to contain a liquid (FIG. 4B). The back-side scanning configuration can be more suitable for larger sensors since the information scanned will be dependent on the surface area used to mount the sensor. In another embodiment of the present invention, the support member is hollow and the active side of the sensor is facing down into the support member where the walls and the sensor create a well in which liquid can be contained. In this example, a separate window is not necessary since the scanning is performed from the back of the sensor. In one aspect of the present invention, the sensor peg can be assembled into a cartridge by welding, adhesive, screws, or other attaching methods. In one preferred embodiment the support member includes countersink holes (106) for screws to assemble the support member onto the cartridge as shown in FIGS. 4A and 4B. In this example, the support member also includes an o-ring (102).

According to one aspect of the present invention, the inlet (107) and outlet (108) ports can be on any of the sides of the cartridge: front, back or any of the other sides. One example, of the location of the inlet (107) and outlet (108) is shown in FIG. 4A.

Experiments were performed to show that the hybridization intensity results of the scanned microarrays from a sensor cartridge with a sensor peg were comparable to those results from a standard embodiment of a biological probe array that may for example include what is generally referred to as a GeneChip® probe array.

Sensor Plate

Figure 5:
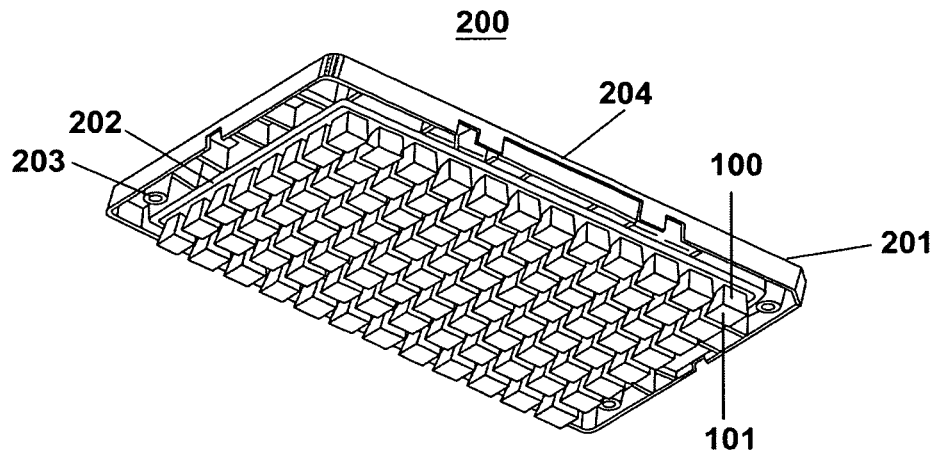
FIG. 5 depicts a microarray plate with a plurality of microarray pegs.

According to one aspect of the invention, a sensor plate (200) as depicted in FIG. 5, includes a holding device (201) wherein the holding device has a plurality of support members (100) which can be for example pegs, projecting from one side of the holding device (i.e. 96 pegs). In a preferred embodiment, the sensor plate further includes a plurality of sensors (101) wherein the sensors are microarrays attached to the end of the support members (100). In one embodiment of the invention, the sensors are attached directly onto the holding device with and without support members. This can be performed with a low-fluorescence adhesive, welding or other attaching methods. In another embodiment of the application, the sensors can be attached to a surface of the support members which can be substantially flat with regard to the surface of the support member. The attachment of the sensors to the supporting members can be performed before or after the support members are attached to the holding device. The array plate can be made of any material which can withstand high temperatures for hybridization and can be stored in cold temperatures for storage (i.e. cyrolite, Hi-Lo acrylic, etc.). In a further embodiment of the invention, the sensor plate includes a sealing surface such as an elastomeric seal (202), alignment features (203) and a clamping feature (204). An advantage of having an elastomeric seal as part of the sensor plate is not having to have an elastomeric seal on multiple mating plates (for example, hybridization plate, shipping plate, reagent plate, detection plate, packaging plate, etc.). In another preferred embodiment, the elastomeric seal is a gasket.

A holding device material can be made from any material that is compatible with the chemical reactants and solvents that are placed in the wells. Any of a variety of organic or inorganic materials or combinations thereof, may be employed for the holding device including, for example, metal, plastics, such as polypropylene, polystyrene, polyvinyl chloride, polycarbonate, polysulfone, etc.; nylon; PTFE, ceramic; silicon; (fused) silica, quartz or glass, and the like. In a preferred embodiment, the material of the holding device is transparent. The holding device (201) may be of any shape. The shape of the holding device can take on various forms, for example, a rectangular, square, circular, oval, and so forth. The dimensions of the holding device can be sufficient to allow for a desired number of support members and sensors of a predetermined size to be incorporated onto the holding device. The holding device can be formed by machining, molding, mechanical forming, and the like. Preferably, the dimensions of the holding device are about 10 mm to about 400 mm in length, about 10 mm to about 400 mm in width, and about 0.25 mm to about 25 mm in depth.

In circumstance where the reaction requires high hybridization temperature and cold temperature storage, the holding device can be made of any material which can withstand high temperatures for hybridization and be stored in cold temperatures for storage (i.e. cyrolite, Hi-Lo acrylic, polycarbonate, etc.).

In one preferred embodiment, the sensor plate (200) includes a holding device (201) and a plurality of sensor pegs (103), wherein the sensor pegs are described above.

The holding device (201) and the support members (100) can be from a single injected mold, where the attachments of the microarrays are then attached to the array plate. In another preferred embodiment of the invention, a sensor plate (200) includes a plurality of sensor pegs wherein the end of the support members of the sensor pegs are attached to a holding device. An example of a holding device is shown in FIG. 5 where the surface on which the sensor pegs are supported is flat. The advantages of having a system with a holding device and separate sensor pegs are: (1) manufacturing flexibility, (2) in-process inspection, (3) possible additional venting space to eliminate bubble formation, and (4) various peg profile designs.

In one aspect of the present invention, array pegs are attached to the holding device. First, a sensor peg is assembled by bonding a microarray to a support member. A low-fluorescence adhesive at the working emission wavelengths of the hybridized, labeled probe arrays can be used to bond the back surface of the microarray to the top surface of the peg such that the probes on the microarray are not damaged. In one preferred embodiment, the curing process can be performed through the top surface of the microarray, from the side, or a combination thereof to bond the microarray to the support member.

In another preferred embodiment, the holding device material is transparent such that the adhesive connecting the sensor peg to the plate can be light cured from the bottom, through the holding device. In a particularly preferred embodiment the material of the holding device is a plastic, Lexan HP1, which is a transparent material that can allow the sensor plate to withstand high temperatures for hybridization, and cold temperatures for storage.

The holding device of the sensor plate or sensor cartridge can be designed such that various sizes of sensors (101) on the support members can be attached. The design of the holding device can also be customized to fit various sizes of sensors. In some embodiments, the holding device can be made of an optically clear/transparent material such that the transparency characteristic can assist in the manufacturing of the sensor plate. The support members can also be made of a dark, light absorbing material to minimize the fluorescence background during scanning. The transparency of the HT plate facilitates the determination of a sample being present.

According to one aspect of the present invention, a method is provided for constructing a sensor plate. A plurality of sensors is produced by dicing a substrate. Plates and support members having a first end and a second end are provided. First, a sensor from the diced substrate is attached to the first end of a support member. Next, the second end of the support member is attached to a plate. These steps are repeated until the desired sensor plate is produced. In a preferred embodiment, the sensors are microarrays and the support members are pegs.

In one embodiment, a method further includes the attaching steps as bonding steps using a curable low fluorescence adhesive. According to another aspect of the invention, the adhesive is cured with a solid state narrow wavelength light source. In a preferred embodiment, the light source is a blue LED. More preferably, the LED's wavelength is from 430 nm to 480 nm and most preferably, the wavelength is approximately 455 nm.

Sensor Strip

Figure 6A:
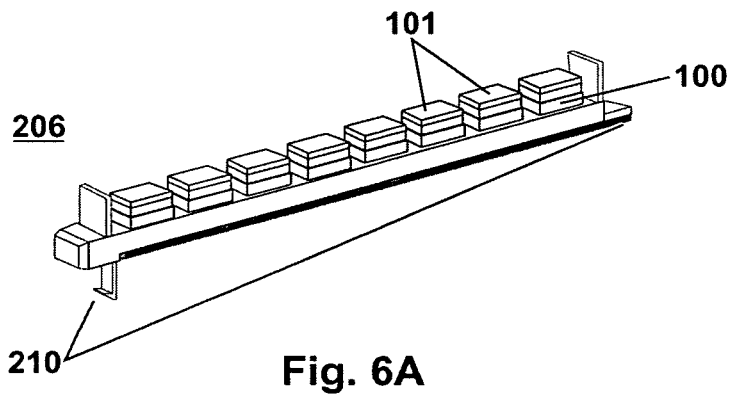
FIG. 6A shows an uncovered sensor strip and FIG. 6B shows a covered sensor strip with sensor pegs.
Figure 6B:
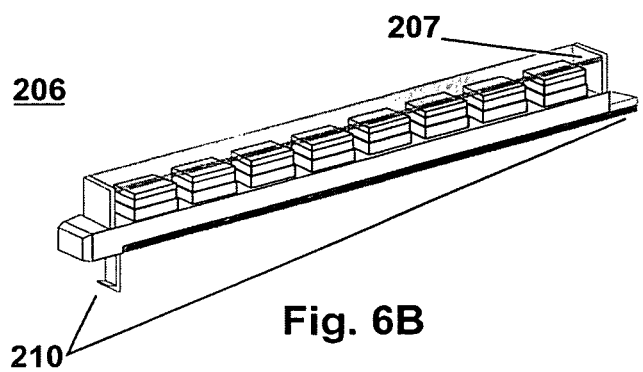

A sensor strip (206), as depicted in FIGS. 6A and 6B, includes a plurality of sensors (101), for example, at least 4, 8, 12, 96 sensors (101) where the sensors may be arranged in a row. In a preferred embodiment, a sensor strip can include a plurality of sensor pegs. Preferably, the number of sensors on a sensor strip is from 8 to 12 sensors. To allow for sensor strip consumption flexibility, a gasket can be incorporated into a sensor strip. The sensor strip can also include a cover (207) as shown in FIG. 6B.

In another embodiment of the present invention, the sensor strip (206) can also include a plurality of sensor cartridges (110). FIG. 7A shows a cross sectional view of a sensor strip of front-side scanning sensor cartridges (refer to FIG. 3B for details of the sensor peg) and FIG. 7B indicates a cross sectional view of a sensor strip of back-side scanning sensor cartridges (refer to FIG. 4B for details of the sensor peg).

In another preferred embodiment, the sensor plate (200) can be a holding device with a plurality of sensor cartridges. Sensor strips can be assembled onto a holding device (201) to combine a plurality of sensor strips to form a sensor plate. The sensor strip includes a plurality of sensor cartridges. According to one aspect of the present invention, a sensor strip can be assembled via snaps or latches (211). There can be attaching mechanisms to attach a sensor strip to another component as shown in FIGS. 6A and 6B. These attaching mechanisms can be any type of method to attach one part to another. For example, a latching mechanism (210) as shown in FIG. 6A and 6B can be used to attach the sensor strip in FIG. 6A to the holding plate (201) in FIG. 8A by connecting to the mating parts (211). In this example, a part at one end of the sensor strip can be fitted into the mating part while a hook at the other end of the sensor strip is pressed into the mating part and locks into place. In addition, the attaching mechanism can include a feature that assists in aligning the part into the mating part (see indentation in the mid section between mating parts (211) in FIG. 8A. FIG. 8A shows a holding device (201) with one sensor strip (206) of 8 sensor pegs attached. The user of the sensor plate has the option of processing one or more sensor strip at a time. FIG. 8B shows a sensor plate of a plurality of covered sensor strips (206) with one strip exposed. A cover (207) can protect the sensors from contamination while the other sensors are being processed.

IV. Immersion Array Plates for Interchangeable Microtiter Well Plates

HT Plates

In another aspect of the invention, the system for processing array plates includes various other plates such as a hybridization plate, washing plate, staining plate, detection plate, reagent plate and packaging plate. The number of wells in an HT plate can be at least as great as the number of sensors to be tested on the sensor plate. The wells are generally coplanar with the surface of the holding device in which the well openings are arranged. The planar openings of the wells may be of any shape such as, for example, rectangular, square, circular, oval, elliptical, rectangular or square with rounded corners and so forth. The bottom of the wells may be level, conical, or slanted as discussed more fully herein. The planar dimensions of the opening of the wells are dependent on the planar dimensions of the sensor aligned with the well opening. Preferably, the planar dimensions of the well openings are about 0.5 mm to about 40 mm in length and about 0.5 mm to about 40 mm in width, more preferably, about 1 mm to about 30 mm in length and about 1 mm to about 30 mm in width. By way of illustration and not limitation, some examples of typical planar dimensions for length and width are about 23 mm by about 54 mm, about 23 mm by about 29 mm, about 6 mm by about 23 mm, about 10 mm by about 13 mm. Preferably, the volume capacity of the wells is about 100 ml to about 300 ml, more preferably, about 1 ml to about 100 ml. In one embodiment, the holding device with the wells is similar to a standard microtiter plate, which is used for high throughput analysis, such as, for example a 24-, 96-, 256-, 384- 864- or 1536-well plate.

HT Assembly

The assembly and removal of the sensor plate to the hybridization plate may be performed with a mechanical device. The holding device may have a feature along the border that facilitates the connection to a HT plate, for example, a latching or unlatching mechanism.

It is desirable to have a seal between the perimeter of the surface of the support member connected to the sensor and the surface of the holding device of the wells comprising the well openings. Various approaches may be employed. In one approach, a flexible member can be utilized to form the seal. Preferably, the flexible member is a gasket and the cross sectional shape of the gasket may be, for example, rectangular, or square with straight sides and a flat, concave or convex bottom, and the like. The flexible member maybe, for example, made of elastomer, rubber, flexible plastic, flexible resins, and the like and combinations thereof. Preferably, the thickness of the gasket is not a problem and there is no deleterious effect on the liquid samples from the flexible member material. In any event the flexible material should be substantially inert with respect to the liquid samples in the wells. Preferably, the dimensions of the gasket are 1 mm to about 5 mm deep and about 1 mm to 5 mm wide, more preferably, about 3 mm deep and about 3 mm wide.

There are several ways to form a seal with a gasket between the sensor plate and the hybridization plate such that the sample does not evaporate and mix between the wells. The gasket can be part of the sensor plate, the HT plate or a separate piece like a clam shell device. The gasket can be formed around each well; however this will require a certain thickness around each well to contain the gasket. Experiments were performed to verify that the samples in the wells would not mix with each other if the gasket was formed around a plurality of wells. The clamping mechanism can be with screws, latches, or other type of clamping mechanism.

Hybridization Plate

Figure 9:
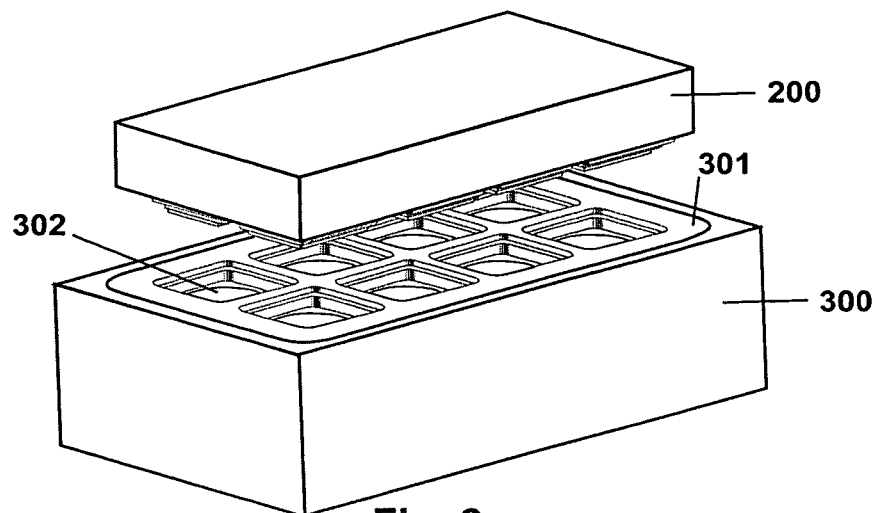
FIG. 9 depicts a hybridization assembly.

According to one aspect of the invention, a hybridization plate (300), as depicted in FIG. 9, includes a sealing surface (301) such as an elastomeric seal between the sensor plate (200) and the hybridization wells (302) when the hybridization plate and a sensor plate are assembled for the hybridization process to create the hermetic seal necessary for high temperature incubation. The sealing surface (301) can be made of any material known in the art such as an elastomeric over-mold seal. The use of this seal onto the design hybridization plate also facilitates separation when the sensor plate assembly is removed from incubation. The design of the wells of the hybridization combined with the design of the support members of the sensor plate assists in reducing hybridization target volumes thus minimizing cost for processing the sensor plates. A hybridization plate (300) can include a plurality of wells (302), for example, at least 2, 4, 8, 12, 96 wells where the wells may be arranged in a row or a matrix. The shape of the hybridization plate may be, for example, rectangular, square, diamond, circular, oval, and so forth. The dimensions of the hybridization plate are sufficient to allow for a desired number of wells of predetermined size to be incorporated into the holding device. The wells are formed in the holding device by machining, mechanical forming, molding, embossing, stamping and the like. Preferably, the dimensions of the holding device are about 2.54 cm (1") to about 12.7 cm (5") in length, about 2.54 cm (1") to about 8.89 cm (3.5") in width, and about 0.63 cm (0.25") to about 1.27 cm (0.5") in depth. By way of illustration and not limitation, an example of typical approximate dimensions for length and width of substrates, is about 12.7 cm (5")×about 12.7 cm (5").

Figure 10A:
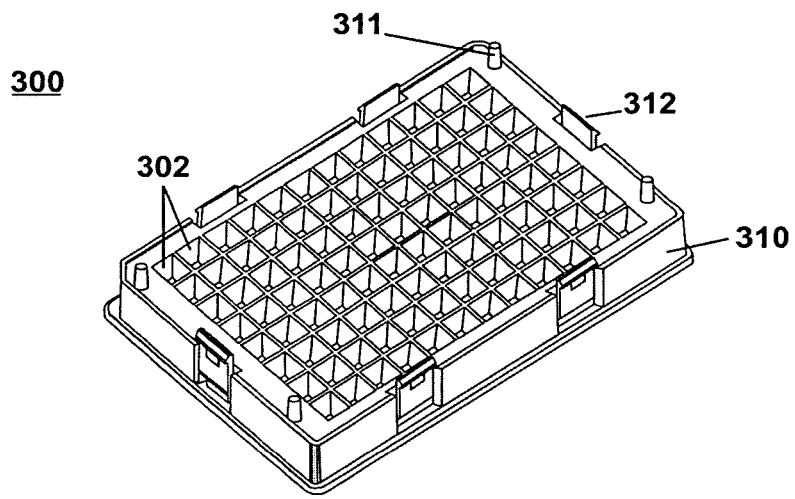
FIG. 10A shows a top view and FIG. 10B shows a bottom view of the hybridization plate.
Figure 10B:
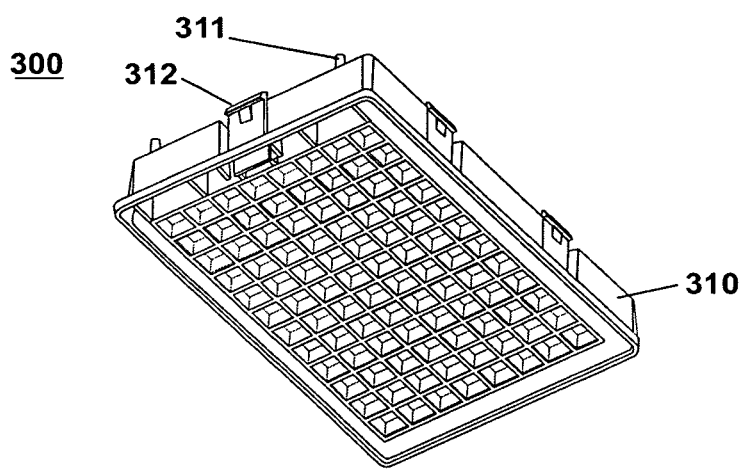

As depicted in FIGS. 10A and 10B, in a further embodiment of the invention, a hybridization plate (300) is designed to minimize fluidic volume introduced during hybridization as well as to minimize the depth spacing between the well bottom and the array surface when the sensor pegs (103) of the array plate are inserted. In one embodiment of the invention, hybridization plate is a plate (310) with a plurality of wells (302) that has alignment features (311) and clamping features (312) along the borders of the plate which assist in the assembling and clamping of the array plate with the hybridization plate for the hybridization process. The hybridization plate can be made from any material that is compatible with the chemical reactants and solvents that are placed in the wells and can sustain high temperatures such as a high temperature molded plastic material (i.e. polycarbonate, polypropylene, etc.). In a preferred embodiment of the present invention, the hybridization plate is made out of Lexan HPI which is chemically resistant and allows the hybridization plate to withstand high temperatures for hybridization, and cold temperatures for storage. This material enables hybridization conditions at temperatures in excess of 60° C. In a further embodiment of the invention, the hybridization plate is suitable for chemiluminescence.

Figure 11:
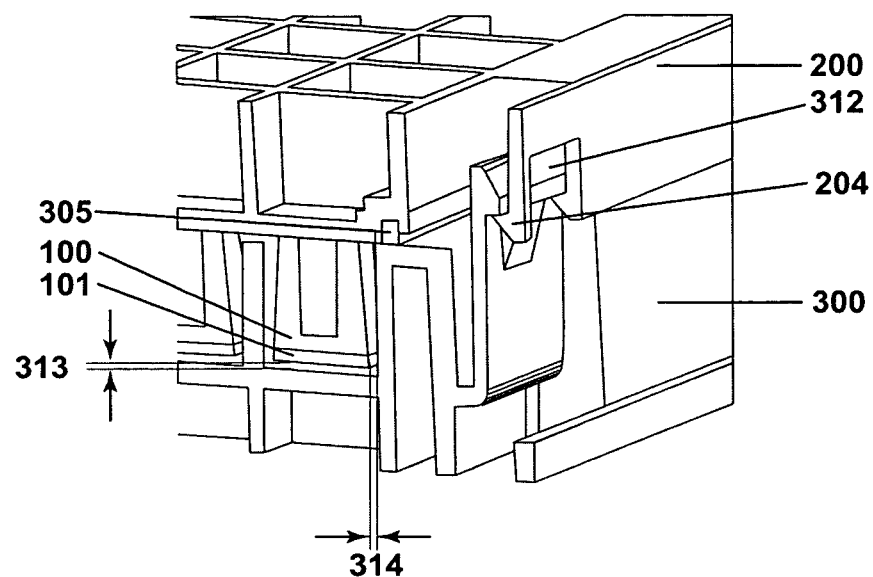
FIG. 11 depicts a close up view of the details (i.e. clamping features, sample gap, well gap, etc.) in a hybridization assembly.

In another preferred embodiment of the invention, an HT assembly as depicted in FIG. 11 includes a sensor plate (200) wherein the sensor plate is an array plate with a gasket (305) wherein the gasket surrounds the plurality of support members and an HT plate (300) wherein the HT plate is a hybridization plate as described in the previous section without a sealing surface such as a gasket. The gasket on the sensor plate (200) surrounds at least all of the support members that are to be in contact with the sensors. The placement, shape, dimensions, or design of the flexible member can be dependent on the dimensions of the holding device, operating temperature and vapor pressure of the liquid sample contained in the wells and so forth. Preferably, the placement of the gasket from the edge of the holding device surface is about 1 mm to about 10 mm. The gasket may also be formed on the holding device by any standard technique such as, for example, over molding, bonding with a pre-formed part, machining and the like. In a preferred embodiment, the sensor plate includes a gasket that is made of any material known in the art such as a Thermal Plastic Elastomer (TPE) over-mold seal and the like.

Furthermore, the sensor plate can further include a plurality of clamping features (204) wherein the features connect to a plurality of corresponding clamping features (312) on the hybridization plate to assure that the pieces are connected. In addition, the alignment pins on the hybridization plate fit in the alignment hole on the sensor plate to verify that the assembly of the sensor plate to the HT plate is consistent relative to the orientation and the placement accuracy. The HT plate can be a hybridization plate, an assay plate, a detection plate or a shipping plate which are all described in detail below. Preferably, the dimensions of the sample gap (313), as shown in FIG. 11, which is the distance from the bottom of the support member to the bottom of the well can be between 50 microns to 3,000 microns, more preferably between 200 microns to 2,000 microns, most preferably about 700 microns in distance. Preferably, the dimensions of the well gap (314) which is the distance from the side of the support member to the side wall of the well can be between 50 microns to 3,000 microns in distance, more preferably between 200 microns to 2,000 microns, most preferably about 900 microns in distance. In some embodiments, a HT assembly is designed such that a hybridization solution volume of less than 100 µl can be used, more preferably about 80 µl and most preferably 50 µl.

In one embodiment of the invention, the sensor plate (200) and hybridization plate (300) is contained by using a clam shell. The clam shell is a box that consists of a gasket and screws. The sensor plate and the hybridization plate can be assembled and placed into the clam shell. The clam shell is closed and the screws are manually or automatically tightened to form a hermetic seal.

In another embodiment of the invention, the gasket described above can be surrounding the sensor, for example, on the sensor plate or sensor strip. The gasket can be around one or more of the sensors. The gasket can be on the device in which the sensor is being assembled with, for example, the hybridization plate, stain plate, reagent plate, detection plate or package plate.

According to one aspect of the invention, a gasket is not required. In one preferred embodiment, the sensor plate can be positioned with the active surfaces of the sensors facing up. The solution can be dispensed onto the active surface. A hybridization plate can then be used to enclose the solution. In one preferred embodiment, the hybridization device can be a plate with features that assist in spreading the solution across the active surface and to minimize evaporation. One example of a feature can be a design of a square within a square, where the inner square is raised a certain height to allow for the desired volume and spread of the solution. The shape of the features will depend on the shape and size of the active areas on the sensors.

Stain Plate

Figure 12:
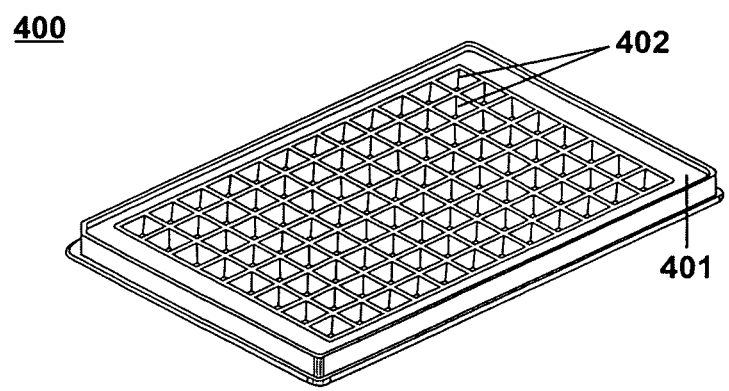
FIG. 12 depicts a stain plate.

An exemplary stain plate (400), which is used for staining the sensor plate (200) during the staining process as illustrated in FIG. 12, is a plate (401) with wells (402) designed to receive the microarray plate. The staining plate includes at least two wells optimized for well depth to use the minimum volume of sample desired.

Wash Plate

Figure 13A:
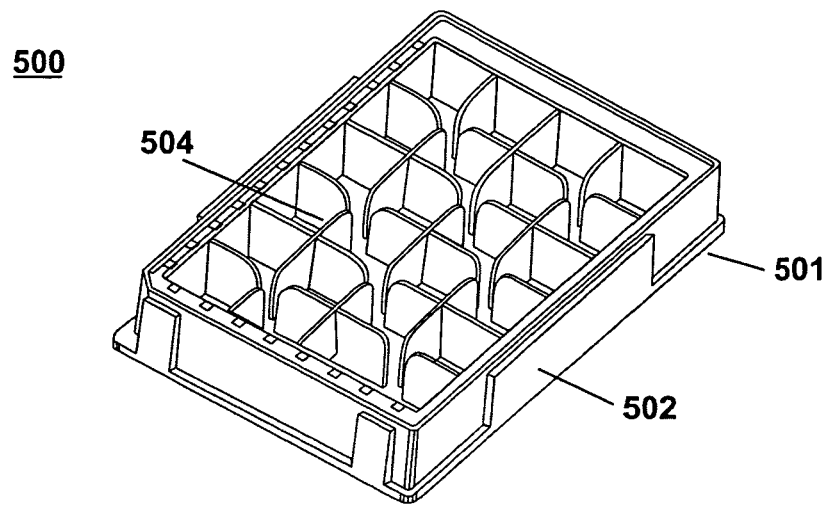
FIG. 13A shows a top view and FIG. 13B shows a bottom view of the wash plate.
Figure 13B:
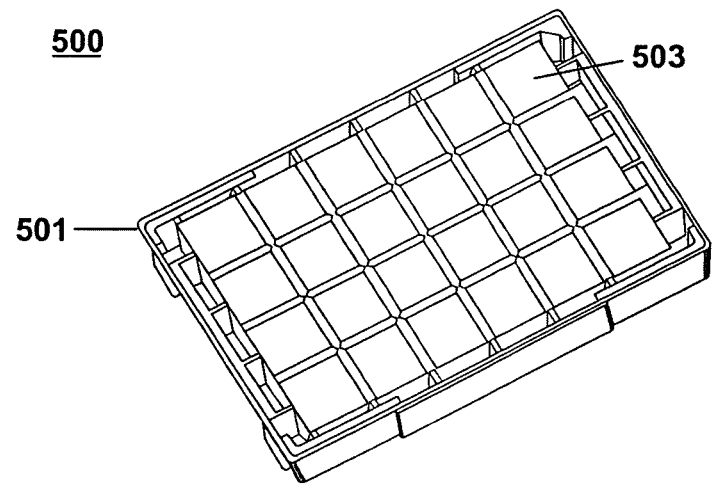

An exemplary wash plate (500) which is used for washing the sensor plate (200) during the washing process as illustrated in FIGS. 13A and 13B is a plate (501) with wells (502) designed to receive the microarray plate. The washing plate includes at least two wells optimized for well depth to use sufficient amount of volume to efficiently wash the sensor(s).

In a preferred embodiment, a wash plate is provided for an open well design where the fluid is dispensed equally across all the wells. An example is shown in FIG. 13A. The partition (504) is optimized to improve the washing efficiency between the pegs. The partition can include vents or slits on the walls to promote even fluid flow across all the wells. Opening up the wells is desired such that the wash solution is contained in the wells. In one embodiment of the invention, there are 24 wells to contain 96 sensor pegs (4 sensor pegs per well). In another preferred embodiment of the invention, there are no wells.

In another preferred embodiment, the wash plate includes a flat bottom (503) as shown in FIG. 13B to assist in controlling the wash process temperature by enhancing the heat transfer across the device. In a preferred embodiment, there can be no walls except grids to provide rigidity to give the part the flatness required for heat transfer with maximum surface contact. Preferably, the height of the grid can be about 0.13 mm (0.005") to full depth of the wells about 2.54 cm (1").

Detection Plate

Figure 14A:
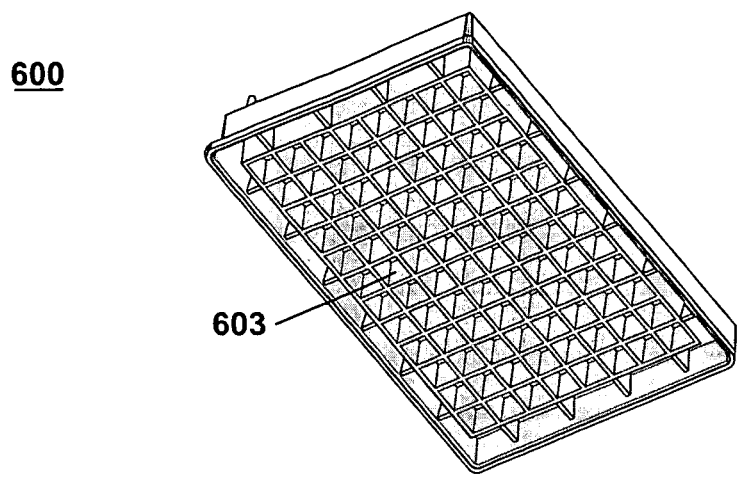
FIG. 14A shows a bottom view and FIG. 14B shows a top view of the detection plate.
Figure 14B:
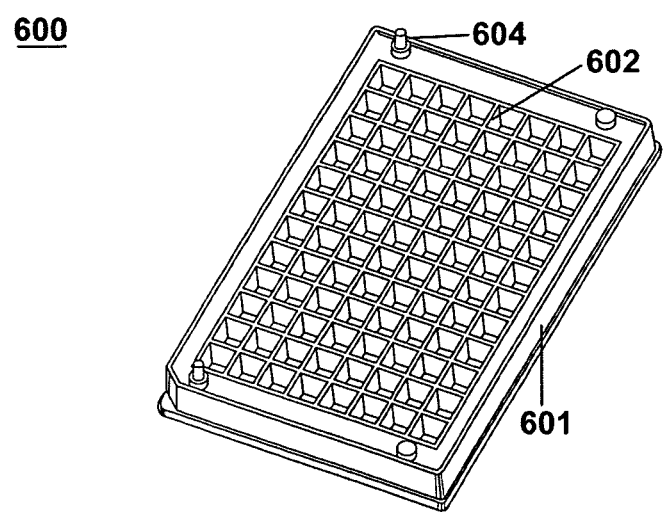

The detection plate (600), which is used for processing the sensor plate (200) during the scanning process, as illustrated in FIG. 14A, is a plate (601) with wells (602) designed to receive the microarray plate. The detection plate as shown in FIG. 14B includes a window of optically clear and low-fluorescence material (603) such as fused silica, zeonor (zionex), etc. After the hybridization process, the microarray plate is transferred to the scanning plate. In one embodiment of the invention, the detection plate has positioning features (604) along the border of the plate for assembly of the microarray plate with the detection plate. The positioning features (604) can assure that the sensor plate is positioned precisely onto the detection plate for high resolution scanning. The positioning features provide a mechanism to align in the x, y and z coordinates. As shown in FIG. 14B, the positioning feature includes a surface to control the z coordinates. In one aspect of the present invention, a plate includes at least two positioning features. Preferably, the dimension of the gap from the surface of the sensor to the optically clear window is between 100 microns to 2,000 microns, more preferably about 600 microns. The optically clear window must be transparent and distortion free for purposes of imaging the surface of the microarrays. It may be desirable that this material is non-fluorescent in order to minimize the background signal level and allow detection of low level signals from low intensity features of the probe array. A multi-plastic molded design can be used to produce the hybridization and detection plates at very low cost. In addition the design can allow for flexibility to change the thickness of the optically clear window material to enhance image resolution of the microarray.

In a preferred embodiment of the present invention, the material of the plate (601) of the detection plate (600) can be black or a dark color to minimize reflection during scanning and the optically clear window is made out of fused silica. The immersed sensors can be imaged and scanned using an array plate scanning instrument through the optically clear window of the detection plate.

Reagent Plate

A reagent plate, which is used for storing and processing the reagents with the sensor plate (200) during the assay process, can include a plate with wells designed to receive the microarray plate. The reagent plate may include a sealable material that maintains the reagent in the wells before use.

Shipping Plate

Figure 15A:
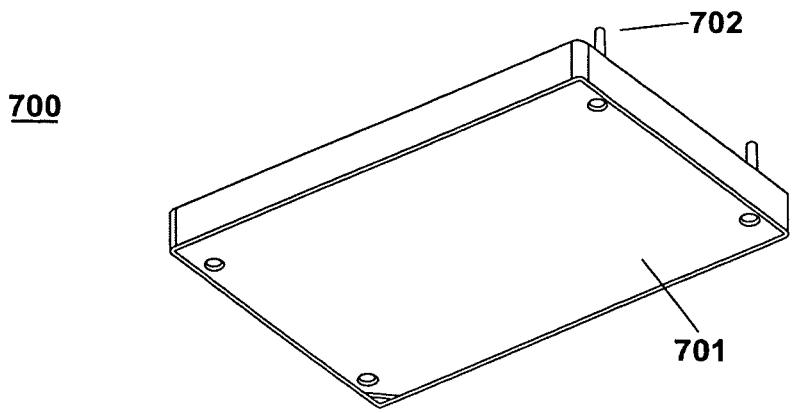
FIG. 15A shows a bottom view and FIG. 15B shows a top view of the package plate.
Figure 15B:
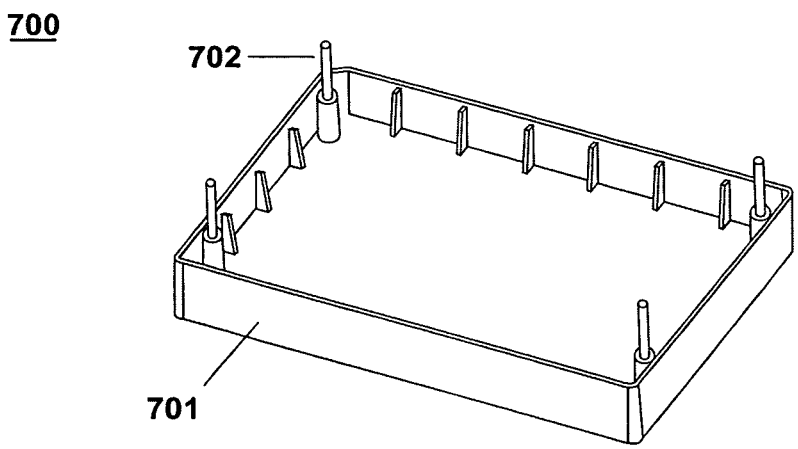
Figure 16:
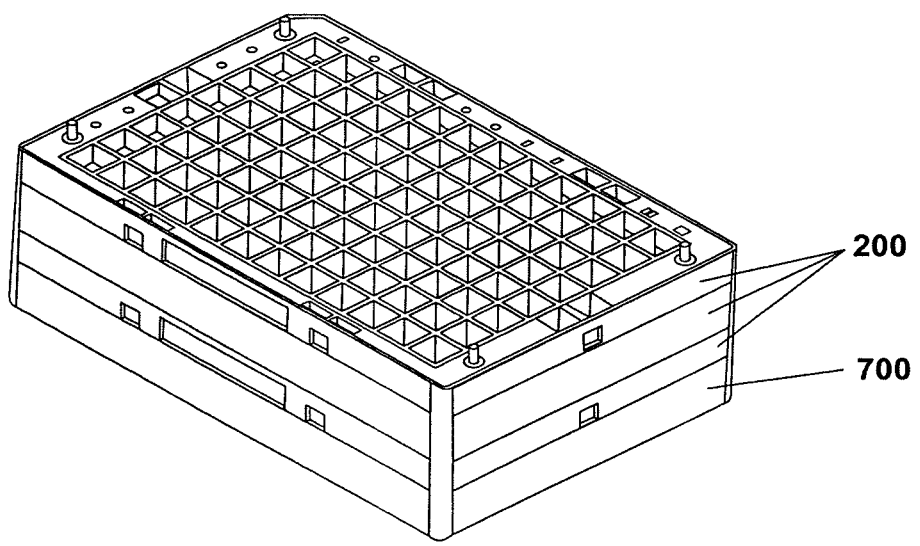
FIG. 16 depicts a stack of sensor plates assembled with a package plate.

Shipping plate (700), which is used for protecting the sensor plate (200) during the shipping process as illustrated in FIGS. 15A and 15B, is a plate (701) with features (702) designed to receive the microarray plate. Microarray plates (200) protected by a shipping plate (700) are illustrated in FIG. 16.

Materials

There are several areas of this design that may require special material capabilities. The non-fluorescence adhesive, the optically clear molded plastic material and the high temperature molded plastic materials for hybridization.

For some applications, an adhesive is used to bond the microarrays to a plastic surface. Because the back surface (non-probe side) of the microarray is the bonding surface, for some embodiments, it is desirable that the adhesive has a low-fluorescence at the working emission wavelengths of the hybridized, labeled probe arrays.

The hybridization well plate is typically used for the high temperature incubation and high stringency wash steps of the array hybridization protocol. With this array plate concept the well plate can be produced with higher temperature plastics to enable hybridization conditions at temperatures in excess of 60° C.

V. Assemble Process

The design of the sensor plate (200) lends itself to high throughput manufacturing processes. One concept is described here and is based on some established available automation processes.

The sensors (101) can be transferred from the dicing film frame to a waffle pack via a high-speed "pick and place" instrument. In one embodiment of the invention, the wafer pack can be designed with pockets for example, located in a 9 mm and 8×12 well layout of a 96 well format. The transferred microarrays can be positioned with the probe side facing down in the waffle pack.

Next, a plate with a plurality of support members or pegs can be pressed (or stamped) onto a pad surface which is coated with wet, uncured adhesive. Then the plate can be pressed onto the microarrays located in the waffle pack. This step is similar to an ink-stamping process used to transfer stamp patterns to a surface.

In one embodiment of the invention, the waffle pack can be designed with openings at the bottom of each pocket with a UV illumination source and a vacuum plenum chamber below to enable the waffle pack to hold the microarrays in position when the plate is pressed on top of the microarrays so as to create a microarray plate. Once the microarray plate is pressed into position, a UV light source is turned on to cure the adhesive. When the adhesive is cured, the microarray plate can be removed with the microarrays permanently bonded. This process takes advantage of a multiple array format to assemble a plurality of microarrays, such as 96 microarrays, simultaneously in order to achieve high speed manufacturing.

In another embodiment of the invention, the microarrays can be transferred from the dicing film frame onto a transfer mechanism which is versatile in holding various sizes of sensor such as a gel pack. The desired microarrays can be selectively picked off the various gel packs which contain various microarray products. The specific microarrays can then be transferred to a waffle pack via a high-speed "pick and place" instrument. The transferred microarrays can be positioned with the probe side facing up and held by a vacuum.

In a preferred embodiment, a diced array can be transferred directly from the film frame (910) to the assembly of a sensor peg. Following this, support members or pegs can be picked up by a Z axis pick up mechanism. Adhesive is then used to cure the sensor to the peg.

Several factors are taken into account in determining a curing process which is used to cure an adhesive during an assembly of a microarray package. It is important to have a curing system that will not damage a feature on the surface of the substrate. Since the corresponding deprotection wavelengths for the reactive groups can range from 300-410 nm, one may want to have a curing process that cures an adhesive at a wavelength that is not within the relevant deprotection wavelength range. In addition, there maybe other layers on a substrate which may include one or more dielectric coatings that can effect the curing method.

A common curing system used in curing adhesives is the UV light curing systems which are well known in the art. Examples of UV light curing systems are spot lights, conveyor systems, flood lamps, and focused beam lamps to cure UV adhesives. Some units deliver a spectrum light concentrated primarily in the UV-A range (320-390 nm wavelength) to achieve curing and others use a combination of medium to high-intensity UV/Visible light and others cure at a low intensity curing of UV/Visible adhesives. In automating the assembly process, one would want to improve the curing process such that it would have a longer life and consistent energy output.

According to one aspect of the invention, a method is provided for curing an adhesive during assembly of a sensor comprising a solid state narrow wavelength light source. More preferably, the solid state narrow wavelength light source is a blue LED having a wavelength which is from 430 nm to 480 nm and most preferably, the wavelength is approximately 455 nm. According to another aspect of the invention, the curing method is used during the assembly of a microarray.

High Intensity Cluster (HIC) Actuator Assembly

The High Intensity Cluster (HIC) Actuator Assembly is a visible solid state, narrow spectrum light adhesive cure system for an automated assembly system to manufacture polymer arrays. The assembly has two main components: the HIC lamp sub-assembly which uses Light Emitting Diodes (LEDs) and the actuator mechanism and mount. In a preferred embodiment, there are two HIC Actuator Assemblies which are mirror image assemblies. These assemblies are integrated onto the main equipment that is designed for high-accuracy die attaching processes, for example, a Micron 5003.

The HIC Actuator assembly (914) provides a unique adhesive curing system for packaging sensors. The LEDs in the HIC Lamp sub-assembly provide the following benefits: on and off is instant, heat is not generated, energy output is consistent, voltage/electrical consumption is very low, emissions is very efficient, lamp life is long (50,000+ hours), efficient output is 100% and it is scalable to any size and non-hazardous.

In a preferred embodiment, an adhesive is formulated such that the adhesive can be cured at a visible wavelength, preferably at a blue wavelength at approximately 475 nm, more preferably at 455 nm. The LEDs have a Lambertian radiation pattern. They emit a narrow bandwidth, blue light with a peak wavelength of 455 nm. Almost all of the energy is between 440 and 480 nm. The nominal average intensity of the HIC Lamp is expected to be equal to or greater than 135 milliwatts/$cm^2$ when measured with a 455 meter.

The number of LEDs will depend on the application. In a preferred embodiment, the LEDs are attached to a U shaped aluminum mount. This mount is attached to an actuator arm with a pneumatic cylinder. The actuator is at an angle so that when the HIC Lamp sub-assembly is extended, it is lower and closer to the die, and when retracted, it is tucked up under the Micron's head with greater clearance. The design allows the sub-assembly to be as close as possible to the die to increase the light intensity during curing. The design also moves the subassembly out of the Micron's Z axes workspace at all other times.

In a preferred embodiment, the configuration has at least 5 HIC Lamp sub-assemblies that are mounted at various non-orthogonal angles in a 'horse shoe' or U shaped layout on a machined aluminum bracket. The HIC Lamp sub-assembly includes a high intensity LED PCB assembly, mounting posts, lens bracket. The bracket also acts as a heatsink for the LEDs. The light from each LED is directed through and focused by two lenses mounted axially in a custom housing. The first lens is a Total Internal reflection collimator lens that gathers up to approximately 90% of the LED's light and directs it in an axial direction. The second lens is a lens that further collimates the light and focuses it at the intended target. In one further embodiment of the present invention, this second lens is a Fresnel lens.

The actuator mechanism is a pneumatically driven bracket mounted to a precision linear bearing. The pneumatic cylinder incorporates two sensors to detect and verify both extend and retract positions. The bearing and pneumatic cylinder are mounted at a 3 degree angle in reference to the horizontal plane. This design allows the HIC Lamp to be retracted tight underneath the head of the Micron tool for clearance when not in use. It also allows the HIC Lamp to come within 1.2 mm of the Overclamp plate during the cure cycle for maximum effectiveness.

The HIC Actuator assembly is installed on the head of the Micron Tool. The HIC Actuator assemblies are bolted to the side of the X xxis front air bearing plate on the Micron Tool. The cables that power the LEDs on the HIC Lamp sub-assembly are routed to the outside of the actuator mechanism and via a cable travel loop to the mounting bracket. The air lines and the sensor cables for the pneumatic cylinders are routed such that they do not interfere with the process.

According to the present invention, this HIC Lamp sub-assembly is used to cure an adhesive that is dispensed on a top surface of a peg to bond an array to the surface. A variety of dispense configurations can be used to dispense the adhesive on a top surface of a peg. An adhesive can be dispensed as one drop, a plurality of drops, a mist, can be dispensed in lines, can be applied by a mechanism to place a layer of adhesive on the top surface, etc. A variety of curing system configurations can also be used to cure an adhesive.

In a preferred embodiment, the present invention has two curing steps. The first step is to tack an array in place onto a top surface of a peg and then continue to complete the cure with a second step. Adhesive is dispensed on the top surface of the peg. The array is then positioned on top of the peg and held in position using vacuum. While the array is held in position, a set of blue LEDs shine light onto the array to cure the adhesive. The adhesive which is exposed from the side of the array is cured and tacks the array in place. The vacuum tip is then retracted and the blue LED configuration is returned to transmit light through the substrate to cure the adhesive beneath the substrate. The parameters, including the delay time to turn on and the total duration cure time, involved in this curing method can be programmed. The LEDs are controlled through digital I/O on the Micron. Custom software on the Micron turns the LEDs on and off based upon the previously defined parameters.

In a preferred embodiment the HIC Actuator assembly design can accommodate curing of adhesive underneath substrates of various shapes with surface areas from 3 to 16 $mm^2$, preferably a square shaped substrate.

According to the present invention, the UBS Matrix Lamp Assembly is a sub-assembly that is used to cure sensor peg (103) to the holding device (201). This UBS Matrix Lamp Assembly incorporates a matrix LED Printed Circuit Board (PCB) assembly for adhesive curing. It also includes two small LEDs that are used for backlighting the two holding device targets: a hole and a slot.

The holding device is loaded into position onto the UBS Matrix Lamp Assembly. The two tapered precision guide pins on the UBS Matrix Lamp Assembly engage the two alignment holes features on the holding device and position it for contact with the Overclamp Plate. The compressible gasket located on top of the UBS Top plate provides compliance when contacting and pushing against the bottom surfaced on the holding device (201). This is necessary due to the inherent tolerances of the molded holding device (201) when attempting to control the planarity of the holding device's mating features.

The two back light LEDs on the UBS Matrix Lamp Assembly provide a means of illuminating the critical reference features on the holding device (201). After the holding device (201) is lifted into place, the two small LEDs turn on and the Arm Camera on the Micron moves over the position of each feature to find the locations of the features with the integrated vision system. This will establish the origin, X and Y axes, and rotation of the holding device (201) for assembly.

The adhesive is dispensed onto a specific location on the holding device (201) where the sensor peg (103) is going to be bonded. Sensor peg (103) is picked up and placed by vacuum onto the dispensed adhesive. Once sensor peg (103) is placed into position, a light source from the bottom of the transparent plate is turned on. The light shines through the plate and cures the adhesive while the sensor is held in position relative to the plate.

In a preferred embodiment, 96 high intensity LEDs are arranged in a matrix of 12 columns and 8 rows. The LEDs have their anodes attached to one of the column traces on the PCB and their cathodes to one of the row traces. There are several configurations in which the LEDs can be activated: all at once, a plurality at a time, etc. In a preferred embodiment, each LED is individually activated by providing a low voltage power to the column and a return path through the row. The high intensity LEDS in the matrix will turn on based upon the selection of peg placement in the Micron's Place Program.

After the assembly process is completed, the UBS Matrix Lamp Assembly is lowered back down and the assembled holding device (201) drops back into the Auer carrier. The conveyor section then transports the carrier out of the Micron.

According to one aspect of the invention, an apparatus is provided to reduce pitch and roll variations used during an assembly of a sensor package. The apparatus which has an x axis plane, y axis plane, and a z axis plane also has a plurality of adjustable kinematic features. One of the adjustable features is a fine pitch adjuster that transverse in the z axis plane. Other adjustable features are spherical kinematic features which are fixed in the nominal z axis plane and provides for rotation around the x and y axes by adjusting the adjustable features to reduce the pitch and roll variations of the sensor package to be assembled. According to another aspect of the invention, a method is provided for wherein the pluralities of adjustable kinematic features are adjusted at the same time. More preferably, an adjustable kinematic feature is a threaded mechanical device.

According to one aspect of the invention, a method is provided for assembling a sensor into a sensor package wherein a positioning of a plurality of datum points on the sensor package relative to a reading surface of the sensor is maintained throughout the assembly such that the sensor is in proper position when the sensor package is inserted into a reader. A plurality of pre-assembled sensor pegs are provided, where a sensor is attached to a first end of the sensor peg, providing a reading surface and at least one section of a second end of the sensor peg is substantially flat to be able to be attached to a holding device wherein the holding device has a plurality of datum points. A plurality of holding devices is provided, where the holding device has a first side and a second side and where the first side has a plurality of defined areas. An assembly tool is provided to assemble the sensor peg to the holding device by maintaining the datum points as a reference target. The datum points on the holding device are measured to characterize the holding device to obtain the reference position to be maintained by the assembly tool. An adhesive is dispensed onto the defined area of the holding device. The sensor peg is positioned on the holding device such that the second end of the sensor peg is in the adhesive and the reading surface is in relative alignment with the datum points of the holding device using the reference target of the assembly tool. The adhesive is cured to bond the sensor peg to the holding device. The providing, dispensing, positioning, and curing steps are repeated to bond the sensor pegs onto the holding device to assemble the sensor package with the aligned reading surface of the sensor to the datum point of the holding device.

According to another aspect of the invention, a method is provided to assemble a sensor into a sensor package, where the holding device is a plate and the sensor package is a sensor plate. More preferably, the sensor plat is an array plate. In a preferred embodiment, the datum points of the array plate include three locations.

According to one aspect of the invention, the assembly method uses an inspection system (915) with a camera to locate and measure the datum points. In another aspect of the invention, the assembly method uses a Z height sensor to locate the reading surface of the sensor. More preferably, the Z height sensor is a laser sensor.

According to one aspect of the invention, the adhesive is formulated such that the adhesive is cured with a solid state narrow wavelength light source. In another aspect of the invention, a solid state narrow wavelength light source is used to cure the adhesive while the sensor and holding device are in alignment relative to the reference of the assembly tool. More preferably, the solid state narrow wavelength light source is a blue LED and most preferably, the solid state narrow wavelength light source is a plurality of blue LEDs. In a preferred embodiment, the adhesive is cured from the second side of the holding device, where the holding device is transparent.

Electronic Batch Record

In high volume manufacturing of sensors, electronic batch records can be used to keep track of the high volume of components and data. The system requires that each sensor is tracked and accounted for. The product, the wafer number, the plate number, and the peg location of the plate are examples of what information can be recorded and tracked. The system is flexible such that it can accommodate various circumstances that can complicate the tracking of information. A number of sensors from various wafers or products can be assembled into one plate. There can be a situation where partial wafers are processed and the rest of the sensors from that wafer are stored for further assembly at a later date. All this sensor data and information can be recorded and tracked by a manufacturing tracking software program, for example PROMIS.

In one embodiment of the invention, a final summary report can be generated for the supervisor to review the process and for Quality Assurance to verify and approve the process. There will be a significant amount of data generated and the report will be able to focus on the key information that requires verification and approval. The form of this summary report can be such that the style of the report is similar to a standard manufacturing final paper batch record. This final summary report can be produced by combining the manufacturing tracking software program, for example PROMIS, with a database, for example Oracle, and using a software program, for example Crystal report, to create the manufacturing electronic batch record summary report. This method enables the supervisor to review the process and ensure that all the entries are correct, the signatures of the people who entered the data are captured, that every step is time stamped, and all the proper steps are followed. Quality Assurance then uses the electronic batch record summary report to verify and approve the process.

Another invention is an electronic start up check list. This method provides a check list of tasks that must be completed prior to starting the high throughput sensor assembly process.

In one aspect of the present invention, radio frequency identification detectors (RFID) can be used to assist in tracking the high volume of components. These detectors may be employed in identifying the components of assembly, for example, sensors (101), support members (100), holding devices (201), and sensor plates (200). The RFID can be incorporated into the individual sensors or any other component of the products.

VI. Automated High Throughput Microarray Assembly Systems

One aspect of the present invention provides a system that is made up of individual distinct interchangeable modules that can assemble various types of arrays and package designs. Each module can have at least the same physical inlet and outlet connections (ie. electrical, air, computer, component transferring mechanism, etc.) and a common transport mechanism. The common transport according to the present invention may include a conveyor transport system which can handle a common plate that is compatible with all products to be assembled.

Those skilled in the art will recognize that there are various microarray products and various corresponding assembly processes known in the art that can be applied to the present invention. Accordingly, the present invention is not limited to any particular environment, and the following descriptions of specific embodiment of the present invention are for illustrative purposes only.

Figure 17A:
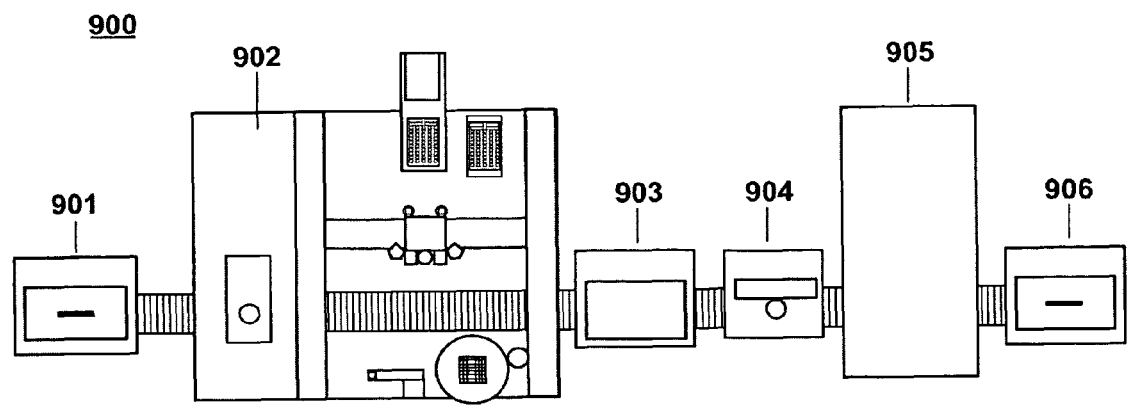
FIGS. 17A depicts a flexible automated microarray assembly system.

In a preferred embodiment, the present invention can illustrate a flexible automated microarray assembly system that can manufacture two different types of microarray products: a sensor cartridge (110) and a sensor plate (200). This flexible automated microarray assembly system (900) is made up of interchangeable modules as represented in FIG. 17A. The various modules can include: facilities, loading, assembly, inspection, printing, labeling, unloading and any other type of assembly related process. Other modules can include curing, etc. The modules, the order of modules, the number of modules, and the placement of modules can vary depending on the product and process steps to assemble the product. In regards to introducing components onto an automated assembly line, the components can be loaded from a different module or a loading mechanism can be incorporated into a first module. In a preferred embodiment, the components for an assembly of a microarray cartridge (110) can include a support having a plurality of diced arrays, an adhesive, and a cartridge. The common components between a microarray cartridge (110) and a sensor plate (200) assembly process are a supply of diced arrays (910) and an adhesive. Therefore, a feeder mechanism to introduce these two components can be built directly onto an assembly module (902). Other components that may be required for assembling a sensor plate (200) assembly is a plate having a plurality of pegs and a holding device (201). Individually designed modules can be provided to supply the uncommon components: a cartridge, a plate, and a plate full of pegs. These modules can be interchanged depending on what products are being assembled. Since an introduction of a plate full of pegs may require additional handling, one may want to build this mechanism directly onto an assembly module.

In one embodiment of the present invention, an assembly of a microarray and a package may include one or more modules. The number of modules can depend on the complexity of an assembly process. According to the present embodiment, a system to manufacture a microarray cartridge (110) can include 6 assembly modules: loading (901), assembly (902), adhesive cure (903), final inspection (904), printing/labeling (905), and unloading (906) which can be represented by FIG. 17A, while the conversion to assembling a sensor plate (200) can include 4 assembly modules: loading (901), assembly (902), final inspection (904), and unloading (906). This flexible automated assembly line can use the same assembly and final inspection modules for both systems.

In one embodiment of the invention, a module can have a plurality and a variety of stations. For example, a sensor plate assembly module (902) can have the following: diced array frame loader (910), Overclamp plate (911), UBS with Matrix LED Array (921), peg assembly station (913), HIC lamps (914), peg inspection (915), peg loader (916), and reject station (917). The placement of the stations on a module will depend on the steps of the assembly process, the space, etc. An assembly module can include a plurality of loading stations depending on the number of parts being assembled. For example for a sensor plate, the loading stations can include a plate loader, diced array loader, peg loader, and an adhesive loader. A loading station can be a specific station on the module platform or a transporting mechanism. For example, the loading station for the peg plates can be a conveyor belt (920). The movements that occur on the module can be controlled by a computer. For example, a keyboard (918) and monitor (919) are indicated in FIG. 17A.

Figure 17B:
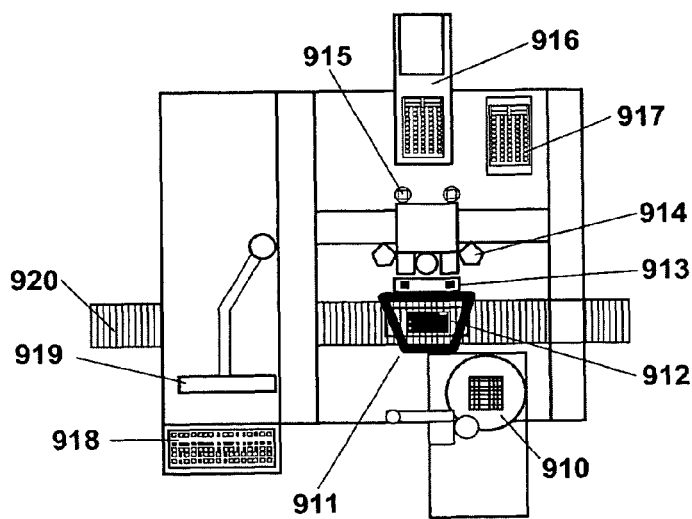

According to the present invention, a method utilizing a precision machined plate to reference the height and position of the substrate, driven by the design requirements of the holding device (201) is provided. The holding device (201) has specific design features that define a horizontal datum or plane. These features mate with similar features in the detection tray (600) used on the scanner, an example of which may include the ImageExpress Scanner available from Axon Instruments Inc. In a preferred embodiment, a holding device (201) is placed into an Overclamp Plate (911) which has mobility in the x, y, and z direction. The Overclamp Plate (911) includes hold down screws, peg station for peg to die assembly, and a peg presence sensor. In addition, a spherical bearing, datum features, swivel pneumatic fitting, and the precision adjustment screw sets. While a holding device (201) is in a holder, a camera analyzes a plurality of datum targets of a sample of plates to obtain a representative baseline. The plate holder is adjusted such that the representative datum points are in parallel with the baseline of an Assembly Module. This will allow the plate that is loaded to be in line with the baseline of an Assembly Module so that any deviations of the molded or machined part can be compensated Next, a support member is picked up from the peg loading station (916) and placed into the peg assembly station (913). Following, a Z laser height sensor finds the height of a support member (100) and dispenses an adhesive on a top surface of a support member (100). Meanwhile, a head picks up a sensor (101) from a diced array holder, locates a target on an array and places an array onto the support members (100) and cures the adhesive. A camera (915) inspects a support member (100) and provides Go/No Go digital input. The head picks up a support member (100) from an Assembly 10 Station and a "Bad" support member (100) assembly can be placed in a Reject Station (917) while a "Good" support member (100) assembly can be moved towards a holding device (201). The adhesive is dispensed onto a plate in an Overclamp Plate (911) where a holding device (201) is aligned to an Assembly Station. The head positions a support member (100) such that an array is held parallel to an Assembly Station. After an array is aligned to a plurality of datum points of a holding device (201), the adhesive is cured. An assembled sensor plate (200) is released and a carrier moves an assembled microarray plate to a final inspection module (904). In another preferred embodiment of the present invention, a plurality of microarrays can be assembled at the same time. An example where two microarrays are being assembled in parallel is shown the Assembly module (902) in FIG. 17B. A method of manufacturing items in parallel is described in U.S. Pat. No. 6,309,831, which is hereby incorporated by reference in its entirety for all purposes.

Figure 18:
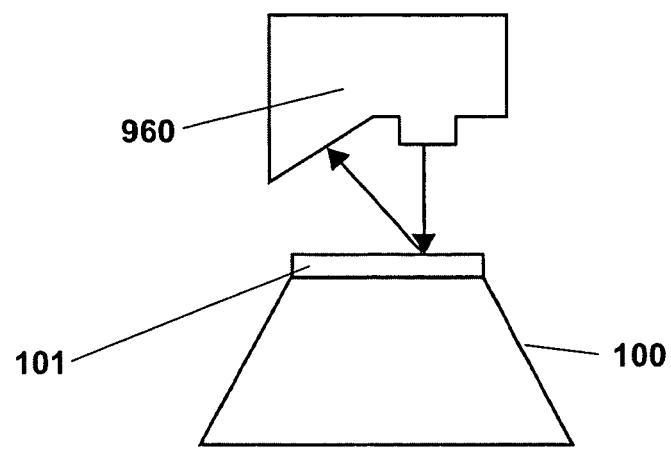
FIG. 18 depicts a laser sensor measuring an assembled microarray.

In another preferred embodiment, a laser sensor (960) measures the pitch and roll of an assembled microarray as shown in FIG. 18. The laser sensor (960) measures the surface of the sensor (101) that is attached to the support member (100) which is bonded to the holding device. The unloading step can involve a specifically designed module based on the product. The specific module can then be switched onto a flexible automated microarray assembly system to unload the specific product.

According to one aspect of the present invention, a flexible automated system is provided for assembling various types of sensors and packages. A plurality of sensors, a plurality of holding devices and a plurality of functional modules are provided. The modules have a common platform and at least one unique assembly step. The plurality of the functional modules is connected to assemble the sensor to the holding device wherein a combination of the various functional modules dictates which sensor and package are being assembled. The automated system is controlled by the software to assemble various types of sensors and packages.

According to another aspect of the invention, a method has at least one type of sensor and a plurality of different holding devices. In a preferred embodiment, the sensor is an array and the holding devices are cartridges and plates. In another preferred embodiment, the combined functional modules are an assembly, a bonding, and a final inspection module.

VII. QC and Testing Methods

In one embodiment of the invention, a device containing a control sensor that may include a plurality of specific hybridization probes to represent a quality of the products produced on an assembly line can be used. The utilization of sensor pegs (103) and holding device (201) will facilitate the QC process. The pre-determined sample of sensor pegs (103), whether it is from one or more lots, can be taken from the process and assembled onto a holding device, depending on the number of sensor pegs. The sample of sensor pegs can be tested all at once to determine which lots can continue the assembly process or whether the corresponding lots are accepted.

In a preferred embodiment of the present invention, a control sensor device can include monomers and possibly a plurality of different feature designs. A wafer is typically diced into individual sensors. A sample of at least one sensor can be designated to incorporate probes to test the quality of the synthesis. In a preferred embodiment, these test probes or control sensors can be collected from various diced wafers and assembled into a sensor plate. The sensor plate allows a plurality of sensors with the test probes to be tested all at once, eliminating the assay variability. The testing parameters, for example, the probes and the assay conditions, can depend on the product. In one aspect of the invention, testing parameters can be developed to determine the optimal testing probes and assay for a plurality of products. Thus, the testing of a plurality of control sensor can be more applicable.

In one aspect of the invention, a wafer is made up of control sensors. The wafer is diced and the control sensors are incorporated into product sensor plates. The control sensor can be a baseline. These chips would eliminate the synthesis variability. These control sensors may include features that are useful in trouble shooting out in the field, calibration, etc. For example, by testing these chips, one can determine whether there was a problem with the particular assay (target, buffer, temp, etc.) by comparing the control chips from another sensor plate.

In another aspect of the invention, the sensor plate can be used as a process development tool. Sensors can be exposed to various process conditions, for example, environmental conditions, process conditions, etc., and then are collected and assembled into a sensor plate. By testing the controls sensors at once, the assay variability can be eliminated in evaluating the process condition.

According to one aspect of the invention, a QC method is provided for assembling a sensor package wherein pre-selected quality criteria is established at each assembly step and is inspected. A pre-selected quality criterion is established per each assembly step. At least one sensor is provided, where the sensor has a first side and a second side wherein the first side has a detectable characteristic. At least one support member is provided to support the sensor wherein the support member has a first side and a second side. A holding device which has a first side and a second side is provided. The first side of the holding device has a plurality of locations. The second side of the sensor is bonded to the first side of the support member. Next the bonded sensor is inspected to determine whether the bonded sensor to the support member meets pre-selected criteria. The bonded sensor and support member assembly which satisfied the pre-selected criteria is then bonded to the holding device by bonding the second side of the support member to the first side of the holding device. Next the bonded support member with the sensor to the holding device is inspected to determine whether the assembly meets pre-selected criteria. The bonding and inspection steps are repeated until the desired sensor package has been assembled. In a preferred embodiment, the QC method is used to assemble a sensor plate, more preferably, an array plate where the holding device is a peg and the sensor is provided by a dicing process.

According to one aspect of the invention, a vision system is used as the inspecting method. According to another aspect of the invention, the assembly of the array to the support member and the support member to the holding device is a bonding process using a curable adhesive. In a preferred embodiment, the adhesive is composed such that the adhesive is cured with the solid state narrow wavelength light source. In another preferred embodiment, the solid state narrow wavelength light source is a blue LED. In another aspect of the invention, a plurality of curing steps is used to bond the sensor to the support member.

VIII. Assay Protocol

The arrays and the liquid samples in the wells are maintained in contact for a period of time sufficient for the desired chemical reaction to occur. The conditions for a reaction, such as, for example, period of time of contact, temperature, pH, salt concentration and so forth, are dependent on the nature of the chemical reaction, the nature of the chemical reactants including the liquid samples, and the like. The conditions for binding of members of specific binding pairs are generally well known and will not be discussed in detail here.

The concept of using separate HT plates for hybridization (and high temperature washing) and scanning enables higher efficiency washes and cleaner images when executing the protocol. In one embodiment of the invention, all three components in the kit (a hybridization plate, a washing plate, staining plate and a detection plate) are disposable so durability and cleanliness is not a requirement beyond its single use. However, since the critical process steps are performed in separate wells, contamination during sequential steps is minimized or eliminated. In addition the transfer of the sensor plates between steps should facilitate more efficient cleaning of the arrays.

The hybridization and high temperature washes are performed in the wells of these HT plates which are designed to be assembled with the sensor plates. In order to minimize the fluidic volume of sample used during hybridization, the sensor plate is designed to minimize the spacing between the immersed array and the well bottom.

Normal washing that does not require high temperature incubation, since wash plates will work at a maximum temperature of 70° C., can be done in standard deep well plates which are also very economical in price since they are commercially available. These commercially available well plates have very large size wells for standard DI water or buffer solutions. Following hybridization and any other steps requiring rinsing or washing, the sensor plates can be immersed into these deep well plates for cleaning. Since the wash fluid volume is large, the cleaning process is more efficient and fewer wash steps would be required, thus saving further process time.

In one aspect of the present invention, the sensor plate (200) is placed into the HT plate (for example, the hybridization plate, washing plate, staining plate, detection plate, reagent plate or packaging plate) filled with the desired liquid to contact the sensor, for example a microarray, with the liquid. In yet another aspect, the sensor peg was used with the active surface of the sensor facing up during hybridization. The buffer or liquid was dispensed directly onto the sensor which was bonded to the support member. In a preferred embodiment, a cover was applied to the dispensed liquid to provide a more uniform layer of liquid across the chip and to reduce evaporation.

In one embodiment of the invention, the sensors from sensor pegs, sensor plates with sensor pegs or with sensors directly attached to the holding device can be used by having the active surface of the sensor facing up while applying a minimal amount of liquid solution. The active surface of the sensors can be facing down during the time where one wants to contact the sensor with larger amount of solution. In still another embodiment, the liquid can be contacted with the sensor by spraying, immersing, or any other known contacting method or a combination thereof.

When sensor plate (200) has completed the hybridization, labeling and washing steps, it can finally be immersed into the detection plate with clean buffer for scanning.

The additional advantage of this sensor plate concept is the ability to implement the same protocol manually by a laboratory technician instead of an automated High Throughput System (HTS) liquid handling instrument. With this interchangeable well plate concept, it could be possible for a single laboratory technician to process for example 96 arrays through the hybridization protocol in approximately the same time to process a few cartridges with the current available tools.

It is understood that any person skilled in the art could understand that there is not a minimum length for the support members of the sensor plate described in the present invention. However, it is inherently understood that there is a practical minimum length. A longer support member may allow simpler washing and staining as it can be immersed deeper.

It is also understood by any person skilled in the art that that there are not limitations as to the size of the sensors attached to the support members of the current invention. For example a 1 mm by 1 mm embodiment of sensor (101) can be mounted on the support members. However, the sensors can be smaller.

In the present invention, a hybridization volume, for example for a 6.3 mm by 6.3 mm embodiment of a sensor (101), can be designed to be about 12 μl. However, there are no design constraints that would prevent a smaller volume. It is also understood by any person skilled in the art, that the detection plate described in the present invention is not volume sensitive. Buffer is used as a coupling fluid between the sensors and the bottom of the detection plate, and its total volume is incidental. However, the distance from sensors to the outside surface of the detection plate may need to be kept very small if the scanner objective lens has a short focal length.

It is further understood by any person skilled in the art, that the transparent window of the detection plate of the present application has a low fluorescence background. In one example, a scanner with no detection plates has a background of 7 counts, which is a unit of measure of the background noise. The detection plate has a total fluorescence background of 14 counts. The dynamic range of the scanner is about 65,000 counts. A maximum acceptable fluorescence background for the window of the detection plate has not been established.

U.S. patent applications Ser. No. 10/325,171 filed Dec. 19, 2002; Ser. No. 10/428,626 filed on May 2, 1003; Ser. No. 10/456,370 filed on Jun. 6, 2003; and Ser. No. 10/738,535 filed on Dec. 16, 2003 describes each different aspects of constructing sensor plates, each of these applications are hereby incorporated by reference herein in their entirety for all purposes.

It is to be understood that the description in this application is and not restrictive. Many variations of the invention will be apparent to those of skill in the art upon reviewing the above description. Various alternatives, modifications and equivalents are possible. The description and figures are by way of illustration and not limitation. One of skill in the art would appreciate that the present invention is not limited to the specific examples provided. In one embodiment of the invention, the system for processing sensor pegs includes various packages such as a sensor cartridge, a sensor plate and a sensor strip. The attached drawings illustrate some of the embodiments of these various sensor assemblies. All cited references, including patent and non-patent literature, are incorporated herewith by reference in their entireties for all purposes.

EXAMPLES

Example 1

The microarray peg (103) as shown in FIG. 1A was designed and assembled. A wafer was diced to provide the microarrays. Various pegs were designed and tested. Bubbles appeared when placing the microarray of a microarray peg into a well with solution. Experiments were performed to eliminate the formation of the bubbles. The peg (100) was design with sloped walls to provide more space for bubbles to evaporate in the chamber. The peg was designed such that it was flushed to the bottom and sides of the microarray to prevent any entrapment of solution during the assay. The microarray (101) was bonded to the wider end of the peg by curing a low fluorescent adhesive. The curing was performed with a blue LED source. Experiments were performed to verify that the shape of this peg prevented the formation of bubbles to occur during hybridization.

Example 2

The micorarray plate (200) as shown in FIG. 5 was designed and assembled to provide a method to process multiple microarrays (101). The microarray plate (200) was assembled by first assembling the microarray peg (103) as described above. Then, the microarray peg was bonded onto the holding plate. These steps were repeated until the desired micoarray plate (200) was manufactured. The holding plate was designed to be rectangular in shape with a substantially flat surface as shown in FIG. 5 to support a plurality of microarray pegs (FIG. 1A). The dimensions were about 25 mm to about 305 mm in length, about 25 mm to about 305 mm in width, and about 1 mm to about 15 mm in depth. The holding plate includes an elastomeric over-mold seal (202) to facilitate the seal used during hybridization and it also facilitates separation when the microarray plate assembly is removed from the hybridization plate or other processing plates. In addition, the microarray plate includes positioning features (203) to assist in placing the microarray plate with the other plates.

In one aspect of the present invention, the microarray pegs were assembled by bonding a microarray onto a peg with a low-fluorescence at the working emission wavelengths of the hybridized, labeled probe arrays to protect the probes on the microarrays. The adhesive was dispensed on the top surface of the peg where the end with the larger surface area was facing up. The microarray was placed on top of the adhesive and the adhesive was tacked in place by curing the adhesive from the side. Then, the adhesive was completely cured through the top surface of the microarraay to bond the microarray to the peg.

In another preferred embodiment, the next assembly step was to bond the microarray peg onto the holding device. In a particularly preferred embodiment, the material of the holding device was transparent such that the curing of the adhesive which bonded the microarray peg to the holding plate can be cured through the holding plate. The adhesive was dispensed onto the desired location on the holding plate. The end of the peg with the microarray was placed in contact with the adhesive and plate. The adhesive bonding the microarray peg and the holding plate was then cured from the bottom, through the holding plate. These steps were repeated until the desired sensor plate was produced.

Example 3

The hybridization plate (300) as shown in FIGS. 10A and 10B was designed to be compatible with the microarray plate (200) as described above. The hybridization plate has alignment features (311) and clamping features (312) along the borders of the plate which assist in the assembling and clamping of the microarray plate with the hybridization plate for the hybridization process.

The shape of the hybridization plate was rectangular and contains the number of wells corresponding to the microarray plate. The wells were formed in the holding device by molding. Preferably, the dimensions of the holding device are about 2.54 cm (1") to about 12.7 cm (5") in length, about 2.54 cm (1") to about 8.89 cm (3.5") in width, and about 0.63 cm (0.25") to about 1.27 cm (0.5") in depth.

The microarray plate was assembled with the hybridization plate by orienting the alignment pins (311) on the hybridization plate with the alignment holes (203) on the microarray plate. The microarary pegs were guided by the alignment features into the wells in the hybridization plate. Once, the elastomeric over-mold seal (202) on the microarray plate was in contact with the corresponding surface on the hybridization plate, the pieces were pressed together until the clamping features locked in place. The dimensions of the peg and the wells were designed such that the fluidic volume introduced during hybridization was minimized. This included minimizing the depth spacing between the well bottom and the microarray surface. After the hybridization, the use of the seal on the microarray plate facilitated the separation when the microarray plate assembly was removed from incubation.

What is claimed is:

1. A method for constructing an array plate comprising:
   dicing a wafer to produce a plurality of arrays of nucleic acids, wherein each array comprises an optically transparent material;
   providing a plurality of individual support members, wherein each individual support member has a first end and a second end, wherein the second end of each individual support member has a substantially flat, solid surface area;
   bonding each array to the first end of each individual support member with curable adhesive to provide a plurality of assembled array-support members, wherein each array is aligned to the first end of each individual support member such that each array covers the entire surface area of the first end and wherein the curable adhesive is cured by shining a light source through the array;
   bonding the substantially flat second end of each individual support member of an assembled array-support member to a substantially flat, solid surface of a plate with curable adhesive, wherein the bonding allows the entire surface area of the second end of each individual support member to be completely bonded to the plate; and
   repeating the bonding steps to produce an array plate.

2. The method of claim 1 wherein the light source is a blue LED having a wavelength of about 430 nm to about 480 nm.

3. The method of claim 1 wherein the light source is a blue LED having a peak wavelength of about 455 nm.

4. The method of claim 1 wherein the bonding steps are repeated to produce an array plate comprising 96 arrays.

5. The method of claim 1 further comprising assembling the array plate with a hybridization plate comprising a plurality of hybridization wells, wherein the distance between each array and the bottom of each hybridization well is about 700 microns.

6. The method of claim 1, wherein the curable adhesive used in each of the bonding steps is the same adhesive.

7. The method of claim 6, wherein the curable adhesive is a low fluorescence adhesive.

8. The method of claim 6, wherein the curable adhesive is cured with a solid state narrow wavelength light source.

9. The method of claim 8, wherein the light source is a blue LED.

10. The method of claim 9, wherein the LED emits light having a wavelength from 430 nm to 480 nm.

11. The method of claim 9, wherein the LED emits blue light with a peak wavelength of approximately 455 nm.

* * * * *